United States Patent
Eger et al.

(10) Patent No.: US 11,202,605 B2
(45) Date of Patent: Dec. 21, 2021

(54) DEVICE AND PROCESS FOR PROVIDING DATA SIGNALS INDICATING MUSCLE ACTIVITIES THAT ARE RELEVANT FOR INSPIRATORY AS WELL AS EXPIRATORY BREATHING EFFORTS OF A PATIENT

(71) Applicant: Drägerwerk AG & Co. KGaA, Lübeck (DE)

(72) Inventors: Marcus Eger, Lübeck (DE); Philipp Rostalski, Lübeck (DE); Herbert Buchner, Nittendorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 509 days.

(21) Appl. No.: 15/779,629

(22) PCT Filed: Nov. 21, 2016

(86) PCT No.: PCT/EP2016/001954
§ 371 (c)(1),
(2) Date: May 29, 2018

(87) PCT Pub. No.: WO2017/092852
PCT Pub. Date: Jun. 8, 2017

(65) Prior Publication Data
US 2018/0344194 A1 Dec. 6, 2018

(30) Foreign Application Priority Data

Nov. 30, 2015 (DE) ............... 10 2015 015 296.3

(51) Int. Cl.
*A61B 5/00* (2006.01)
*A61B 5/389* (2021.01)
(Continued)

(52) U.S. Cl.
CPC ............ *A61B 5/4836* (2013.01); *A61B 5/087* (2013.01); *A61B 5/091* (2013.01); *A61B 5/389* (2021.01);
(Continued)

(58) Field of Classification Search
CPC ........ A61M 16/024; A61M 2016/0042; A61M 2230/40; A61M 2230/60;
(Continued)

(56) References Cited

U.S. PATENT DOCUMENTS 6,588,423 B1    7/2003  Sinderby
10,758,693 B2*  9/2020  Sinderby ............. A61M 16/024
(Continued)

FOREIGN PATENT DOCUMENTS

DE        101 64 446 A1    7/2003
DE   10 2007 062 214 B3    8/2009
(Continued)

OTHER PUBLICATIONS

O'Brien, M. J., Van Eykern, L. A., Prechtl, H. F. R. (1983): Monitoring respiratory activity in infants—a non-intrusive diaphragm EMG technique. In: P. Rolfe (ed.) Non-invasive Measurements, vol. 2, Academic Press, London Ltd., pp. 131-177.
(Continued)

*Primary Examiner* — Devin B Henson
*Assistant Examiner* — Justin Xu
(74) *Attorney, Agent, or Firm* — McGlew and Tuttle, P.C.

(57) ABSTRACT

A device provides a first data signal that indicates an activity of at least one muscle of a patient that is relevant for an inspiratory breathing effort and a second data signal that indicates an activity of at least one muscle of the patient that is relevant for an expiratory breathing effort. The data signals are generated from electromyography (EMG) signals detected by surface electromyography sensors. A computer (Continued)

is configured to determine breathing phase information on the basis of a breathing signal and to check at least one of the electromyography signals or at least one of the separated signals for detectability of a heart signal component and further to assign the signals to an inspiratory breathing activity as well as to an expiratory breathing activity of the patient as a function of the breathing phase information.

19 Claims, 22 Drawing Sheets

(51) Int. Cl.
*A61B 5/087* (2006.01)
*A61M 16/00* (2006.01)
*A61B 5/091* (2006.01)

(52) U.S. Cl.
CPC ............ *A61B 5/7203* (2013.01); *A61B 5/725* (2013.01); *A61B 5/7289* (2013.01); *A61M 16/024* (2017.08); *A61B 5/7221* (2013.01); *A61M 2016/0036* (2013.01); *A61M 2016/0042* (2013.01); *A61M 2230/40* (2013.01); *A61M 2230/60* (2013.01)

(58) Field of Classification Search
CPC ......... A61M 2016/0036; A61B 5/4836; A61B 5/7289; A61B 5/7203; A61B 5/087; A61B 5/091; A61B 5/725; A61B 5/0488; A61B 5/7221
See application file for complete search history.

(56) References Cited

U.S. PATENT DOCUMENTS

| | | | |
|---|---|---|---|
| 2005/0081855 A1 | 4/2005 | Berthon-Jones | |
| 2012/0095742 A1 | 4/2012 | Heyer et al. | |
| 2014/0048072 A1* | 2/2014 | Angelico | A61M 16/0063 128/204.23 |
| 2014/0142395 A1* | 5/2014 | Sattler | A61B 5/0205 600/300 |
| 2016/0262705 A1* | 9/2016 | Swamy | A61B 5/7207 |
| 2018/0235503 A1 | 8/2018 | Derkx et al. | |

FOREIGN PATENT DOCUMENTS

| | | |
|---|---|---|
| DE | 10 2011 016 804 A1 | 10/2012 |
| DE | 10 2007 052 897 B4 | 2/2013 |
| DE | 10 2012 003 509 A1 | 8/2013 |
| JP | 2018527069 A | 9/2018 |
| WO | 2008/131798 A1 | 11/2008 |
| WO | 2015/032504 A1 | 3/2015 |

OTHER PUBLICATIONS

A Generalization of Blind Source Separation Algorithms for Convolutive Mixtures Based on Second-Order Statistics (H. Buchner, R. Aichner, W. Kellermann), in IEEE Transactions on Speech and Audio Processing, Jan. 2005, vol. 13, No. 1, pp. 120-134.
Pan, Jiapu, Tompkins, Willis J., "A Real-Time QRS Detection Algorithm," Biomedical Engineering, IEEE Transactions on, vol. BME-32, No. 3, pp. 230, 236, Mar. 1985.
H. Buchner, R. Aichner, and W. Kellermann, "Blind source separation for convolutive mixtures: A unified treatment," In Y. Huang and J. Benesty (eds.), Audio Signal Processing for Next-Generation Multimedia Communication Systems, Kluwer Academic Publishers, Boston/Dordrecht/London, pp. 255-293, Feb. 2004.
H. Buchner, R. Aichner, and W. Kellermann, "TRINICON-based blind system identification with application to multiple-source localization and separation," In S. Makino, T.-W. Lee, and S. Sawada (eds.), Blind Speech Separation, Springer-Verlag, Berlin/Heidelberg, pp. 101-147, Sep. 2007.

* cited by examiner

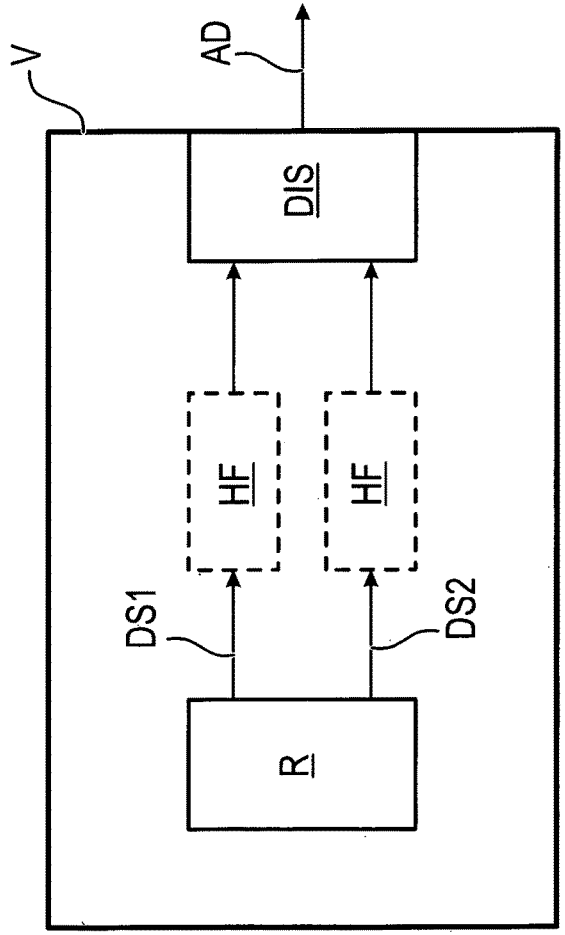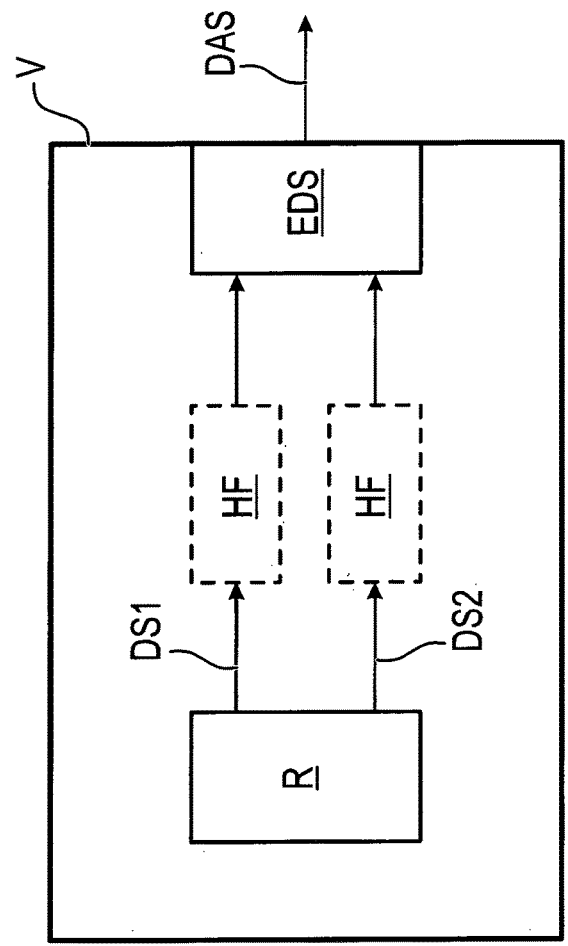
FIG. 19a
FIG. 19b

DEVICE AND PROCESS FOR PROVIDING DATA SIGNALS INDICATING MUSCLE ACTIVITIES THAT ARE RELEVANT FOR INSPIRATORY AS WELL AS EXPIRATORY BREATHING EFFORTS OF A PATIENT

CROSS REFERENCE TO RELATED APPLICATIONS

This application is a United States National Phase Application of International Application PCT/EP2016/001954, filed Nov. 21, 2016, and claims the benefit of priority under 35 U.S.C. § 119 of German Application 10 2015 015 296.3, filed Nov. 30, 2015, the entire contents of which are incorporated herein by reference.

FIELD OF THE INVENTION

The present invention relates to a device for providing a first data signal that indicates an activity of at least one muscle of a patient that is relevant for an inspiratory breathing effort for providing a second data signal that indicates an activity of at least one muscle of the patient that is relevant for an expiratory breathing effort. The present invention further relates to a process for providing such signals.

BACKGROUND OF THE INVENTION

It is known that electromyogram signals, which can be obtained on the skin surfaces of a patient by means of electromyography sensors, can be used for the purposes of respiratory monitoring or else ventilation of a patient. Such processes are known from the sources mentioned below:
DE 10 2007 052 897 B4,
O'BRIEN, M. J., VAN EYKERN, L. A., PRECHTL, H. F. R. (1983): *Monitoring respiratory activity in infants-a non-intrusive diaphragm EMG technique*. In: P. Rolfe (ed.) Non-invasive Measurements, Vol. 2, Academic Press, London Ltd., pp. 131-177,
U.S. Pat. No. 6,588,423 B, and
WO 2008 131798 A1.

Electromyogram (EMG) signals can be obtained, for example, based on surface electromyography sensors, which can be attached to the outer skin surfaces of the patient. As an alternative, this may be achieved by means of electrodes on or in a catheter, for example, a nasogastric catheter, wherein the catheter is inserted by inserting the catheter into the body of the patient. Since the insertion of such a catheter is invasive and may possibly cause discomfort in a patient, it is advantageous to use only surface electromyography sensors, which can be placed on skin surfaces of the patient outside of body openings of the patient, for example, the nose, ear, mouth or rectum.

The goal in such processes is usually and preferably to obtain an electrical potential difference as a corresponding EMG signal, which indicates an activity of a muscle which is relevant for either an inspiratory activity of the patient or for an expiratory activity of the patient, by means of a pair of sensors. In case the breathing activity shown by a muscle that is relevant for inspiratory activity can be detected on the basis of such an EMG signal, then, for example, a signal can, as a result, be visualized or displayed, which gives a clinician information about whether the patient is breathing in spontaneously. Corresponding statements can be made for an expiratory breathing activity.

Further, it may be possible to control a ventilation (also known as a respiration) of the patient as a function of such information based on EMG signals.

Problems are usually that EMG signals detected on the basis of surface electrodes may possibly be distorted or disturbed by disturbances, for example, an EKG signal of the heart in the form of a QRS complex, motion artifacts or other effects in spite of extensive actions.

Further, it is possible that a first EMG signal obtained by means of a first pair of sensors indicates inspiratory muscle activities and that a second EMG signal obtained by means of a second pair of sensors indicates an expiratory muscle activity, the corresponding pairs of sensors being positioned at different points of the skin surface of the patient. However, here, an activity of the muscles that are relevant for inspiratory activity may generate signal components in the second EMG signal that shall indicate the expiratory muscle activity, and vice versa, by means of so-called cross-talk of the first signal. Hence, it is important to counteract the above-mentioned disturbances after obtaining the EMG signals.

Typical muscle groups, which cause or generate an inspiratory activity, are, for example, the upper diaphragm, the lower diaphragm or the external intercostal muscles (so-called intercostal muscles).

One muscle group, which usually causes or generates an expiratory muscle activity of the patient, is, for example, the so-called internal intercostal muscles. Other muscles that cause an expiratory activity of a patient are the so-called abdominal muscles.

The above-mentioned effect of the so-called cross-talk is hence due to the fact that action potentials have to be transmitted to muscle fibers in case of contraction of a motor nerve cell for stimulation of the contraction of a muscle. A wave-like propagation of such action potentials in the muscle fibers occurs at a propagation rate of, for example, 4 m/sec to 6 m/sec, so that a propagation delay is not even negligible in the EMG signals. The propagation of such an action potential in a wave-shaped manner to or from a certain muscle may even also be detected at another skin surface position or sensor position within the framework of another EMG signal detection of another muscle, which then precisely represents the so-called cross-talk component at the corresponding other EMG signal.

DE 10 2007 062 214 B3 discloses a process, in which a plurality of electromyography signals can be detected, in order to then suppress a possible unwanted signal or a heart signal component by means of a filtering in each individual signal and to then subject the filtered signals to a correlation to an airway signal in order to assign one of the filtered signals to a breathing activity.

The document "*A Generalization of Blind Source Separation Algorithms for Convolutive Mixtures Based on Second-Order Statistics*" (H. Buchner, R. Aichner, W. Kellermann), in *IEEE Transactions on Speech and Audio Processing*, January 2005, Vol. 13, No. 1, pp. 120-134 discloses a process for a blind source separation of P input signals for obtaining P output signals.

SUMMARY OF THE INVENTION

An object of the present invention is to derive at least two data signals, which indicate an activity of at least one muscle that is relevant for an inspiratory breathing effort or an activity of at least one muscle that is relevant for an expiratory breathing effort from EMG signals detected by means of surface electromyography sensors. The above-mentioned disturbances shall be counteracted hereby.

The object according to the present invention is accomplished by a device as well as by a process as well as by a program. The device provides a first data signal indicating an activity of at least one muscle that is relevant for an inspiratory breathing effort and a second data signal indicating an activity of at least one muscle that is relevant for an expiratory breathing effort.

The device has a first interface, which is configured to detect at least three or more than three electromyography signals of particular pairs of surface electromyography sensors. Further, the device has a second interface, which is configured to detect a breathing signal, which indicates a breathing activity of the patient.

The device further has a computer, which is configured to determine breathing phase information on the basis of the breathing signal, the breathing phase information indicating first time windows of inspiratory breathing activity and second time windows of expiratory breathing activity. Further, the computer is configured to determine at least three separated signals on the basis of the electromyography signals.

The computer is further configured to check whether a heart signal component is detectable in one of the separated signals and to select the corresponding separated signal if a heart signal component is successfully detected.

The computer is further configured to determine the data signals by means of assigning at least one subset of the remaining separated signals to an inspiratory breathing activity as well as to an expiratory breathing activity of the patient as a function of the breathing phase information.

The device further has a data interface, which is configured to provide the data signals.

The device according to the present invention is advantageous because the data signals provided are not determined solely with knowledge of the electromyography signals, but because the determination takes place as a function of the breathing phase information determined on the basis of the breathing signal. Thus, the determination of the data signals which indicate the inspiratory or expiratory muscle activity takes place with a higher reliability because the breathing phase information derived from the breathing signal is used for this determination. Further, the proposed device is advantageous because the data signals are not only obtained solely on the basis of the separated signals, but because a heart signal component that may be present is detected in the separated signals and then a detection of the heart signal component leads to a corresponding signal of the separated signals being selected. An influence of a heart signal component can hereby be minimized or possibly even eliminated.

The device according to the present invention thus operates with a greater accuracy than processes, which do not let breathing phase information on the basis of a breathing signal have an effect on the determination of the data signals, but only on the basis of electromyography signals and following filtering or separation algorithms, which derive data signals.

This device according to the present invention is further advantageous because, by using a higher number of EMG signals, i.e., three EMG signals or more than three EMG signals, a more accurate determination of the data signals, which indicate the inspiratory or the expiratory muscle activity, is possible, wherein, based on the checking of the separated signals for a heart signal component, it is further possible to select that separated signal or to exclude that separated signal as an inspiratory or expiratory data signal, in which the heart signal component is detectable or is essentially present.

The device according to the present invention further preferably has a third interface for outputting display data to a display unit as a function of the data signals. This embodiment of the device according to the present invention is advantageous because display data can be provided by means of this interface, which display data can then be displayed in a display unit for a clinician, so that the clinician can obtain knowledge about the time phases at which a patient has his own inspiratory breathing activity and his or her own expiratory breathing activity.

The device according to the present invention is preferably further characterized in that the device has a ventilator (also known as a respirator) for the ventilation of a patient, and that the computer is further configured to actuate the ventilator as a function of at least one of the data signals. This embodiment of the device according to the present invention is advantageous because the information about when a patient has an inspiratory or expiratory muscle activity, which information is obtained by means of the data signals, can be used directly to control a ventilation of the ventilator. The usual signals for controlling a ventilation by means of a ventilator for a patient are usually based on so-called flow signals or volume flow signals as pneumatic signals of a patient. If a patient has, for example, an inspiratory activity, then he first draws in an air flow or volume flow from a ventilation tube, wherein a volume flow sensor located in the ventilation tube can indicate a change in the volume flow only if the pneumatic resistances present due to the ventilation tube were overcome by the breathing effort of the patient. Thus, a time delay possibly occurs between the actual inspiratory activity of the patient and the detection thereof on the basis of the volume flow sensor in the ventilation tube. A detection of an inspiratory muscle activity on the basis of at least one of the data signals may be more reliable because the corresponding data signal is based on an EMG signal and an activity of a muscle that is relevant for inspiratory activity in the corresponding EMG sensor signal is indicated earlier than in the volume flow signal that is detected at the same time. As a result of this, a more accurate and more reliable ventilation of the patient can thus be ensured. The data signal, which indicates an inspiratory activity of the muscles of the patient that are relevant for inspiratory activity, can preferably be used for a ventilation triggering. This triggering may then be more accurate than a triggering which is only based on a pneumatic breathing signal or on a volume flow signal.

The device according to the present invention is further preferably characterized in that the pneumatic breathing signal is a volume flow signal, and that the computer is further configured to determine the breathing phase information as a function of the volume flow signal and of at least one preset threshold value. This embodiment of the device according to the present invention is advantageous because by using a threshold value, smaller fluctuations of the volume flow signal are left out of consideration, so that more reliable breathing phase information can be obtained with higher reliability than when no threshold value is used. This is hence especially advantageous because smaller fluctuations of the volume flow signal around the zero value may already occur before an actual inspiratory phase of the patient because of so-called jitter effects, leaks, or else regulation effects of the ventilator, and these are left out of consideration because of the threshold value.

The device according to the present invention is further preferably characterized in that the computer is configured to determine the separated signals by means of adaptive digital filtering of the electromyography signals. This embodiment of the device according to the present invention is advantageous since an adaptive digital filtering of the EMG signals makes it possible to determine the data signals or the separated signals necessary for this not only by means of a rigid filtering, but by letting it run adaptively, which precisely especially takes into consideration changes over time in the so-called cross-talk effects, so that an automated process is available that takes into consideration such changes over time in the disturbances that occur.

The device according to the present invention is further preferably characterized in that the computer is further configured to actuate the ventilator both as a function of the at least one data signal and as a function of the breathing signal, and that the computer is further configured to carry out a quality evaluation of the at least one data signal, and that the computer uses either the at least one data signal or the breathing signal for actuating the ventilator as a function of the quality evaluation. This embodiment of the device according to the present invention is advantageous because it can be decided by means of the quality evaluation of the data signal whether the data signal is sufficiently good in terms of its quality in order to be able to be used for an actuation of the ventilator, or else whether this breathing signal should not be used for this actuation of the ventilator.

The device according to the present invention is further preferably characterized in that the computer is further configured to check the ventilator for a pressure-controlled ventilation support, and that the pressure-controlled ventilation support takes place such that a ventilation pressure occurs at least at times as a function of the at least one data signal. This embodiment of the device according to the present invention is advantageous because a pressure-controlled ventilation support is a usual process within the framework of a ventilation of a patient by means of a ventilator, wherein the ventilation of the patient does not preset the ventilation pressure by means of a preset characteristic, but that the ventilation pressure, with which the patient is being ventilated, can now be adapted to the actual inspiratory or expiratory activity of the patient.

The process according to the present invention is preferably characterized in that it is suitable for providing at least one first data signal and one second data signal, wherein the first data signal indicates an activity of at least one muscle that is relevant for an inspiratory breathing effort and wherein the second data signal indicates an activity of at least one muscle that is relevant for an expiratory breathing effort, comprising:

detection of three or more than three electromyography signals of particular surface electromyography sensor pairs, detection of a breathing signal, which indicates a breathing activity of the patient, determination of breathing phase information, on the basis of the breathing signal, which information indicates first time windows of inspiratory breathing activity and second time windows of expiratory breathing activity, determination of at least three separated signals on the basis of the electromyography signals, checking whether a heart signal component is detectable in one of the separated signals and selection of the corresponding separated signal if a heart signal component is successfully detected, determination of the data signals by means of assignment of the separated signals to an inspiratory breathing activity and to an expiratory breathing activity of the patient as a function of the breathing phase information, as well as provision of the data signals.

The process according to the present invention is further preferably characterized in that it comprises the output of display data to an optical display unit as a function of the data signals.

The process according to the present invention is further preferably characterized in that it comprises the control of a ventilator as a function of at least one of the assigned data signals.

Each of the corresponding advantages, as mentioned before in reference to the various embodiments of the device according to the present invention, applies to the different embodiments of the process proposed above.

A program with a program code for carrying out the process according to the present invention when the program code is executed on a computer, on a processor or on a programmable hardware component is further proposed.

The present invention is explained in more detail below on the basis of the figures on the basis of special exemplary embodiments without limitation of the general inventive concepts. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 19a is a schematic view showing an advantageous embodiment of the device according to the present invention having an interface for the output of display data;

FIG. 19b is a schematic view showing an advantageous embodiment of the device according to the present invention having an external data interface for the provision of the data signals obtained;

DESCRIPTION OF THE PREFERRED EMBODIMENTS

Figure 1:
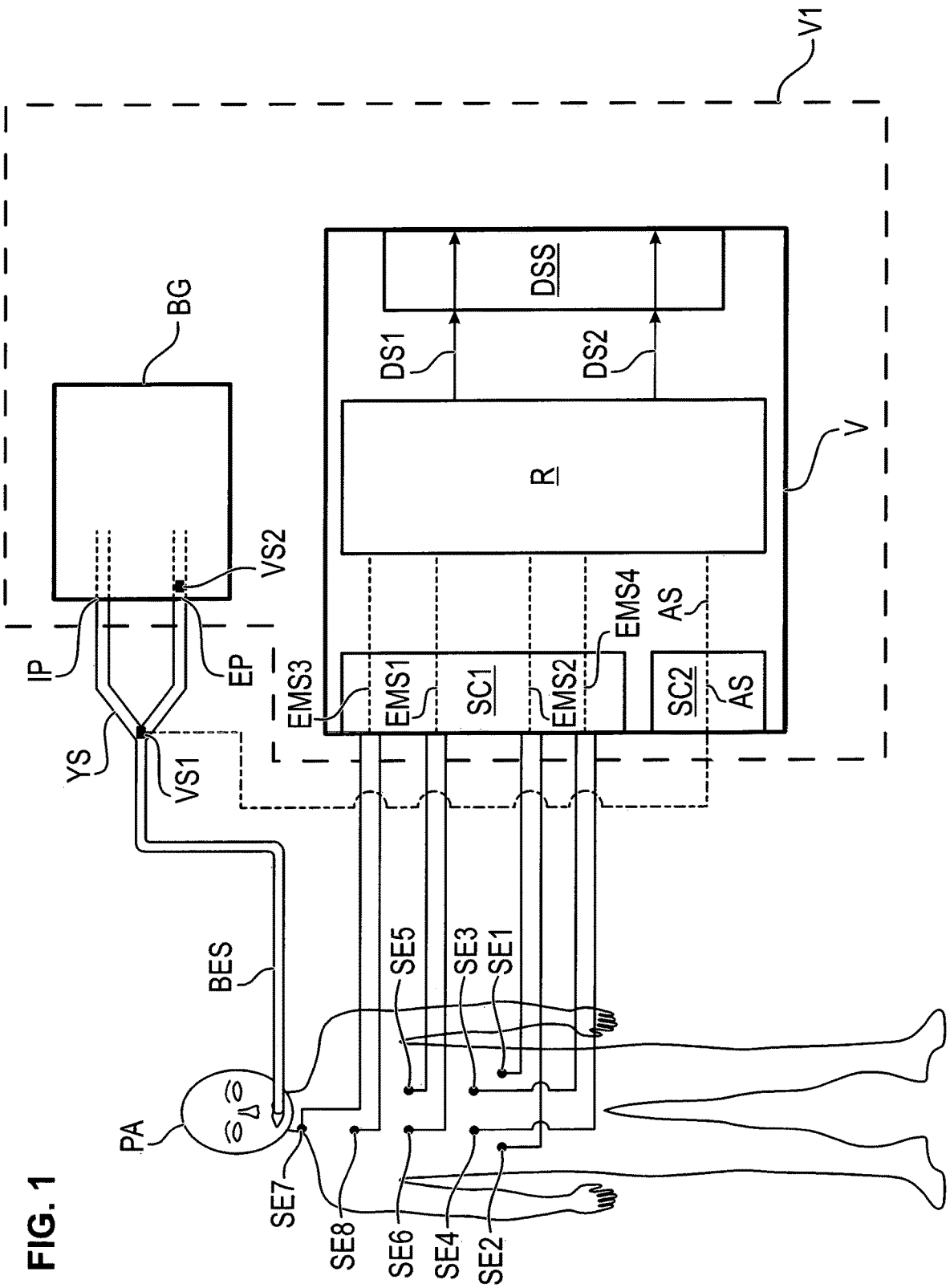
FIG. 1 is a schematic view showing a device according to the present invention as well as a ventilator.

Referring to the drawings, identical reference numbers may designate identical or comparable components in the following description of the attached figures, which only show some exemplary embodiments. Further, summary reference numbers (general designations) may be used for components and objects, which appear multiple times in one exemplary embodiment or in a drawing, but are described jointly with respect to one or more features. Components or objects which are described with identical or summary reference numbers may be identical in terms of individual features, a plurality of features or all features, but may also possibly be configured differently, provided nothing else explicitly or implicitly appears from the description. It should be kept in mind that an element that is shown or described as "connected" or "coupled" to another element may be connected or coupled directly to the other element or that elements lying between them may be present.

FIG. 1 shows the device V according to the present invention as well as a preferred embodiment V1. In the preferred embodiment of the device V1, a ventilator BG is an integral component of the device V1 according to the present invention.

Shown further is a patient PA, to whom is connected a ventilation tube BES, which is connected in turn to an inspiratory port IP and to an expiratory port EP of the ventilator BG by means of a Y-piece YS.

A pneumatic sensor VS1, as an alternative called a breathing signal sensor, is located in the vicinity of the Y-piece YS for detection of a breathing signal AS. The breathing signal sensor is preferably a volume flow sensor. As an alternative to the breathing signal sensor VS1, a breathing signal sensor VS2, preferably likewise a volume flow sensor, may be present at the expiratory port EP or in the vicinity of the expiratory port EP of the ventilator in order to detect a breathing signal. The detection of the breathing signal AS preferably takes place by using sensor signals of two such breathing signal sensors VS1, VS2.

Shown further are different surface electromyography sensors SE1, . . . , SE8, which are positioned or placed at different points of the patient P on his outer skin surface. These surface electromyography sensors are sensors, which can be placed on outer skin surfaces of the patient outside of body openings of the patient, for example, the nose, ear, mouth or rectum.

A particular electromyography (EMG) signal EMS1 is detected by means of a particular pair of sensors SE5, SE6. A corresponding statement can be made for the detection of the shown EMG signals EMS2, EMS3, EMS4.

Figure 4:
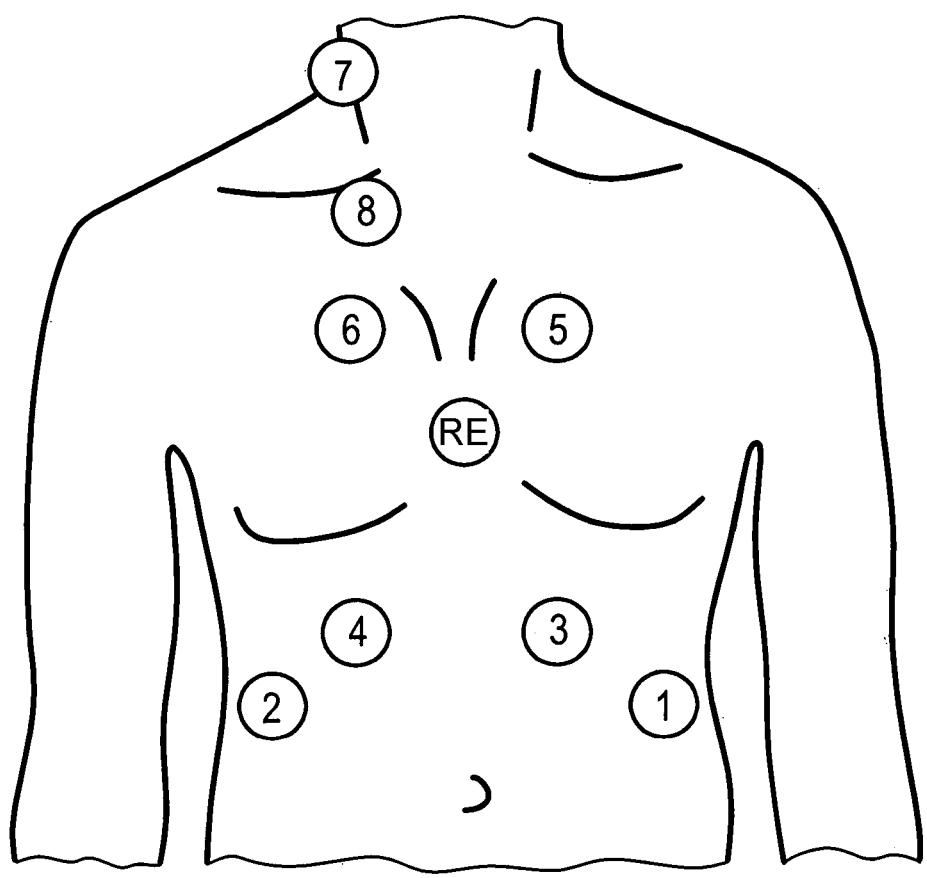
FIG. 4 is a schematic view showing preferred body positions for the positioning of surface electromyography sensors.

FIG. 4 shows preferred electrode positions for the positioning of surface electromyography sensors for the detection of corresponding EMG signals. In this case, an EMG signal is preferably a potential difference between two electrodes of a pair of sensors. Such a potential difference between the electrodes may preferably be determined by referring to a reference potential that is applied to a reference electrode RE.

An EMG signal, which indicates signal components of an internal intercostal muscle, can preferably be obtained by means of a pair of sensors at positions 5, 6. An internal intercostal muscle is a muscle that is relevant for an expiratory activity.

An EMG signal, which indicates a muscle activity of the lower diaphragm, which is a muscle that is relevant for an expiratory breathing activity, may preferably be obtained by means of a pair of sensors at positions 1, 2. An EMG signal which indicates a muscle activity of the upper diaphragm, which likewise indicates a muscle for an inspiratory breathing activity, may be obtained by means of the sensor positions 3, 4.

An EMG signal, which detects a heart signal component, also called EKG signal or QRS complex, can be detected by means of the positions 7, 8. Such an EKG signal or heart signal may be present in the other above-mentioned EMG signals as well, so that the EMG signal obtained by means of the electrodes at positions 7,8 may possibly be used as a reference signal within the framework of a subsequent signal processing.

A detection of an EMG signal, e.g., of the signal EMS1, may preferably take place by means of a corresponding pair of sensors, e.g., the pair of sensors SE1 and SE2. However, as an alternative, a determination of an EMG signal may take place for this such that a single electrode detects a signal potential, and that the EMG signal is then determined as potential difference between this detected potential and a reference potential. The reference potential is preferably a mean potential averaged from a plurality of potentials of a plurality of sensors.

The reference electrode does not necessarily have to be used for the determination of potential differences. The potential of the reference electrode is preferably used with a low-resistance input of a signal amplifier.

The above-mentioned FIG. 1 shows a situation, in which four EMG signals EMS1, . . . , EMS4 are detected. At least two EMG signals EMS1, EMS2 are detected in a first exemplary embodiment of the present invention, as will be explained later in more detail in reference to FIG. 2. Three or more than three EMG signals, preferably four EMG signals, EMS1, . . . , EMS4, are detected in a second exemplary embodiment of the present invention, as will be explained later in more detail in reference to FIG. 3.

The device V, V1 has an interface SC1, by means of which the electromyography signals EMS1, . . . , EMS4 of the particular surface electromyography sensor pairs SE5 and SE6, SE1 and SE2, SE7 and SE8 as well as SE3 and SE4 can be detected. This interface SC1 preferably has an analog/digital converter unit in order to convert the detected EMG signals into digital EMG signals. A reference electrode at position RE from FIG. 4 is not explicitly shown in FIG. 1. However, it is apparent to the person skilled in the art based on FIG. 4 and this description that the interface SC1 of the device V, V1 may also be configured to detect a reference potential by means of an EMG signal of a surface electromyography sensor at position RE in order to then correlate other EMG signals EMS1, . . . , EMS4, preferably all EMG signals EMS1, . . . , EMS4, of other sensors with the EMG signal of the reference potential.

The interface SC1 preferably carries out a removal of a particular DC component in the particular EKG signal EMS1, . . . , EMS4.

The device V, V1 further has at least one additional interface SC2, which is configured to detect the breathing signal AS that indicates a breathing activity of the patient. The interface SC1 preferably has an analog/digital converter unit for the digitization of the detected breathing signal AS.

The device V, V1 further has a computer R.

The detected signals EMS1, . . . , EMS4, AS are preferably provided in digitized form, i.e., scanned and quantified, from the interfaces SC1, SC2 to the computer R within the device V, V1. This preferably takes place within the device V, V1 by means of provided data transmission and data communication means between the individual units SC1, SC2, R, for example, by means of a data bus.

The computer R preferably has a memory unit, in which the detected signals EMS1, . . . , EMS4 as well as AS can be stored in at least some sections and/or at least temporarily in order to be able to then process these signals. Such a memory unit is not explicitly shown in FIG. 1.

The device V, V1 determines at least one first data signal DS1 as well as one second data signal DS2 on the basis of the detected signals EMS1, . . . , EMS4, AS.

The device V, V1 further has a data interface DSS, which is configured to provide the data signals DS1, DS2 obtained. This data interface DSS may either be an external interface, to which the device V, V1 provides the obtained data signals DS1, DS2, to other units outside of the device V, V1. This is thus shown in FIG. 1.

However, this data interface DSS may preferably be a data interface present within the device V, V1, to which the obtained signals DS1, DS2 are provided for the purpose of a further later processing within the device V, V1, so that this data interface DSS does not absolutely have to be an external data interface.

The first data signal DS1 indicates an activity of at least one muscle of a patient that is relevant for an inspiratory breathing effort and the second data signal DS2 indicates an activity of at least one muscle of the patient that is relevant for an expiratory breathing effort.

Figure 2:
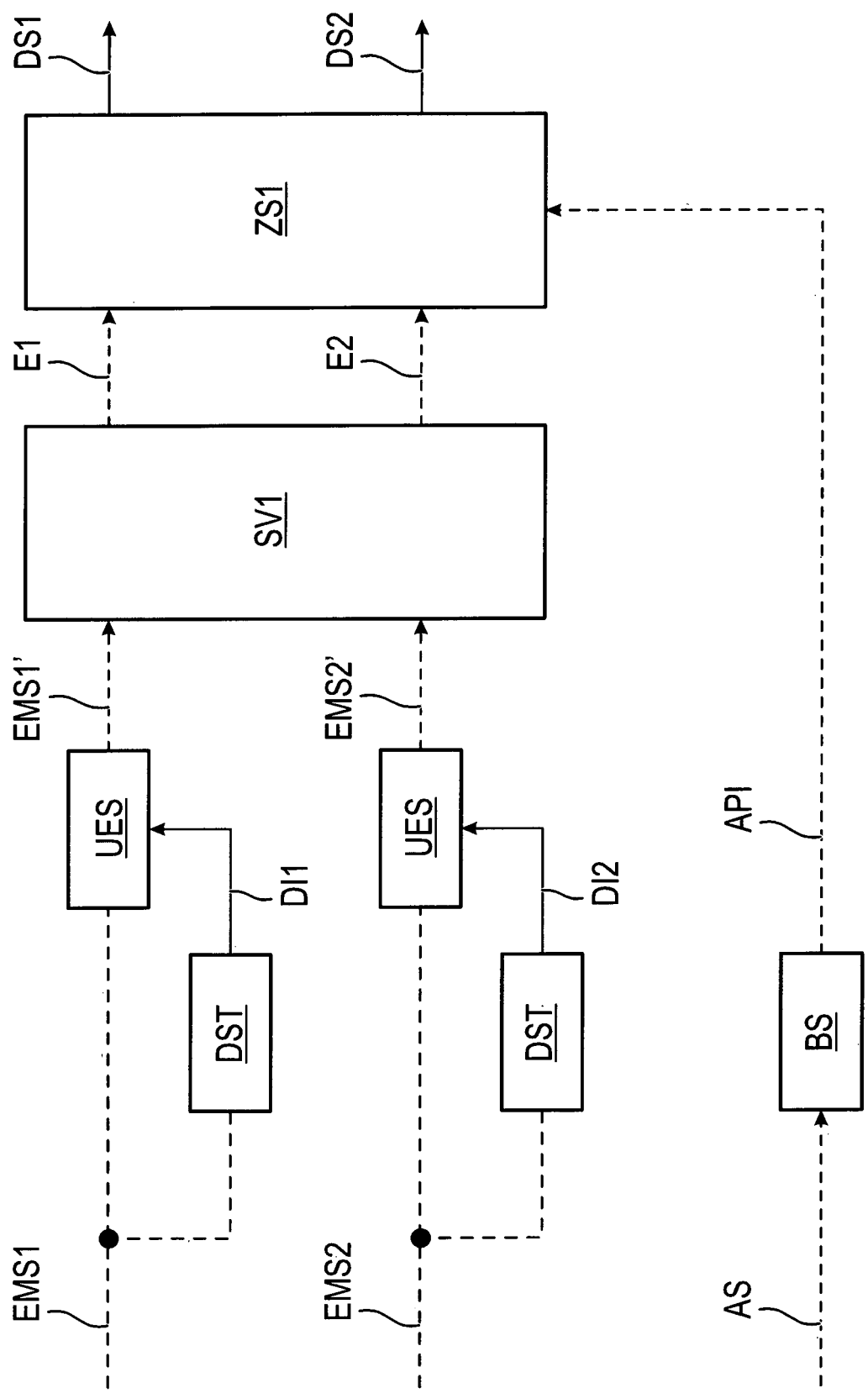
FIG. 2 is a schematic view showing aspects of obtaining the data signals on the basis of EMG signals and of a breathing signal according to a first exemplary embodiment.

FIG. 2 shows steps, which are carried out by the computer R according to the first exemplary embodiment of the device from FIG. 1. The computer is configured to determine the data signals DS1 and DS2 on the basis of two electromyography signals EMS1, EMS2 and the breathing signal AS.

The computer determines breathing phase information API, which indicates first time windows of inspiratory breathing activity and second time windows of expiratory breathing activity, on the basis of the breathing signal AS in a determination step BS. This determination step BS will be explained later in more detail with reference to FIG. 6.

The computer checks the two electromyography signals EMS1, EMS2 each for a particular detectability of a particular heart signal component by means of a particular detection step DST. The detection step DST will be explained in more detail later with reference to FIG. 5. A detection step DST indicates a detectability by means of detection information DI1, DI2.

Further, the computer suppresses a heart signal component detected in an EMG signal EMS1, EMS2 on the basis of the corresponding detection result, or on the basis of the particular detection information DI1, DI2 obtained, in the corresponding EMG signal EMS1, EMS2. This takes place in a particular suppression step UES. Thus, the corresponding, particular and possibly modified EMG signals EMS1', EMS2' are obtained.

Separated signals E1, E2 are determined on the basis of the EMG signals EMS1', EMS2', which in turn are based on the EMG signals EMS1 and EMS2, respectively. A separation of the signals EMS1', EMS2' takes place in a signal processing step SV1 for obtaining the separated signals E1, E2. The signal processing step SV1 will be explained later in more detail with reference to FIG. 7.

The two separated signals E1, E2 obtained are assigned in an assignment step ZS1 to an inspiratory breathing activity or to an expiratory breathing activity of the patient as a function of the breathing phase information API obtained in order to determine the data signals DS1, DS2. The assignment step ZS1 will be explained in more detail later with reference to FIG. 12. Both or all separated signals E1, E2 are thus used in the assignment step ZS1 in this exemplary embodiment.

Figure 3:
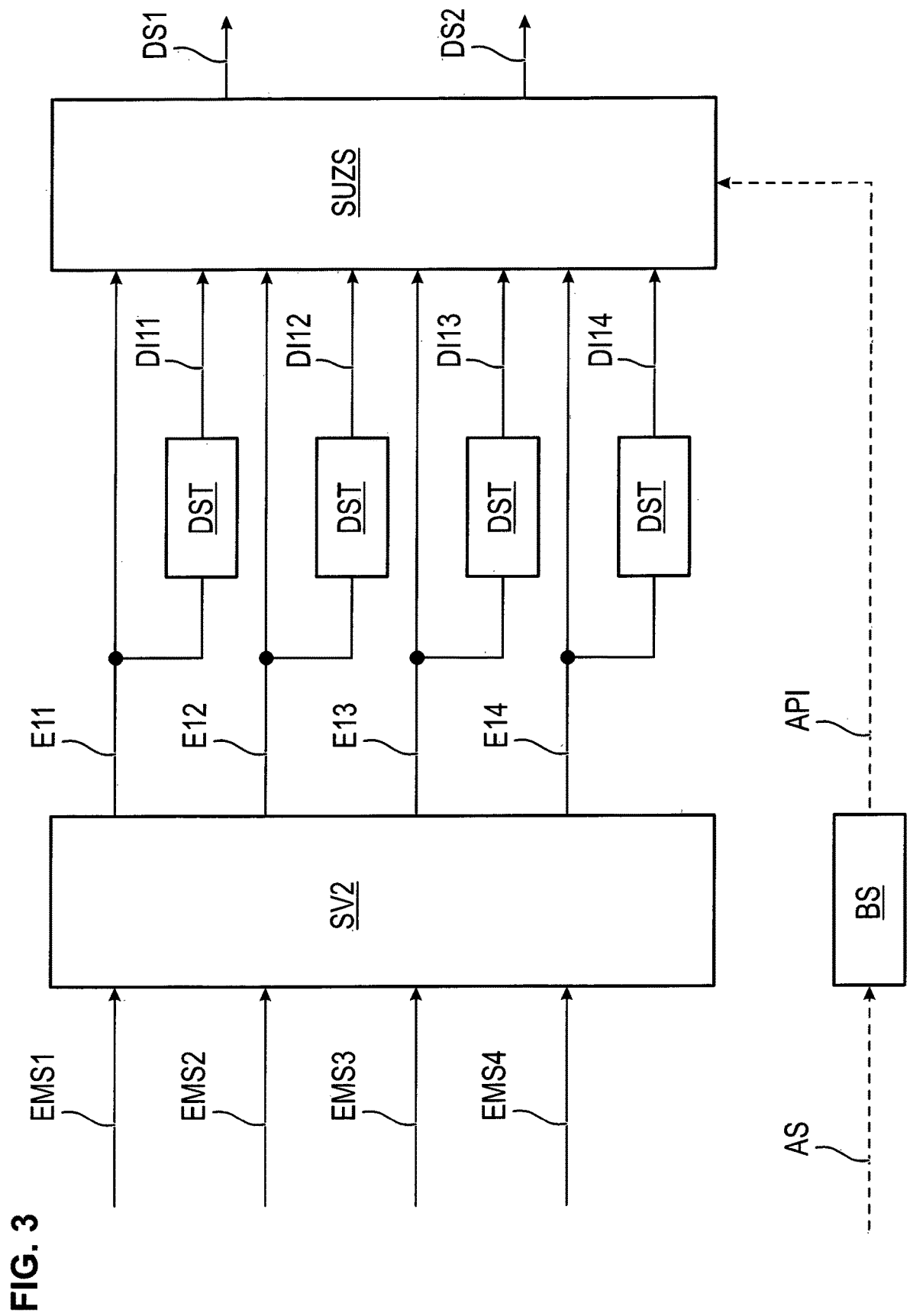
FIG. 3 is a schematic view showing aspects of obtaining the data signals on the basis of EMG signals and of a breathing signal according to a second exemplary embodiment.

FIG. 3 shows a second exemplary embodiment of the present invention, in which at least three EMG signals, in this example four EMG signals, EMS1, . . . , EMS4, as well as the breathing signal AS are detected. The breathing phase information API is derived in the determination step BS analogously to the first exemplary embodiment from FIG. 2 and will be explained later with reference to FIG. 6.

At least three separated signals, in this example four signals, E11, . . . , E14, are determined in a signal processing step SV2 on the basis of the electromyography signals EMS1, . . . , EMS4. The signal processing step SV2 will be explained in more detail later with reference to FIG. 18.

The separated signals E11, . . . , E14 are each checked as to whether a heart signal component can be detected in them on the basis of the detection step DST. Particular detection information DI11, . . . , DI14 for the particular, corresponding EMG signal E11, ..., E14 is obtained therefrom and provided to a selection and assignment step SUZS. This selection and assignment step SUZS carries out a selection of the one separated signal, in which a heart signal component is most detectable in order to then use the remaining separated signals by means of an assignment for the determination of the data signals DS1, DS2. Only one subset of the separated signals is thus used in the assignment step in this exemplary embodiment.

Figure 5:
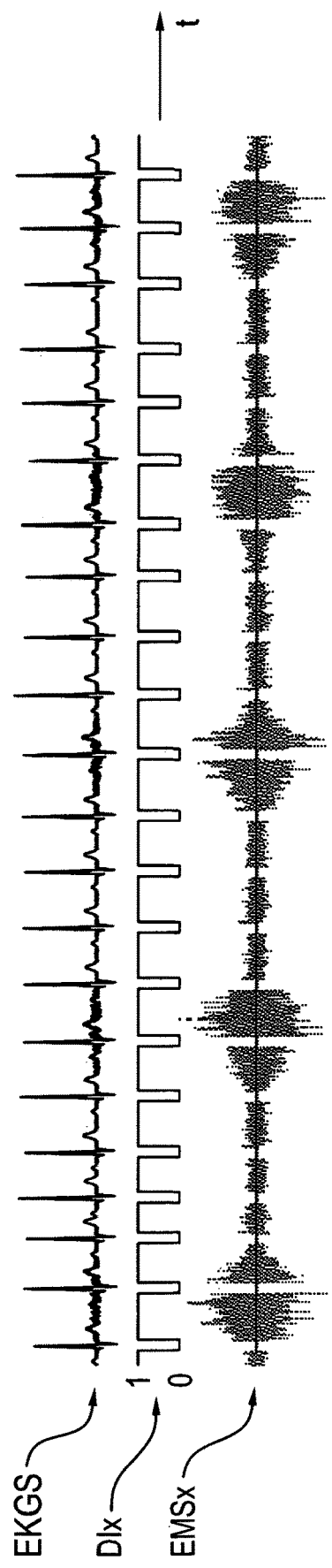
FIG. 5 is a graph view showing exemplary signals within the framework of a suppression of an EKG signal in an EMG signal.

FIG. 5 shows exemplary signals in the course of a detection step DST, as was mentioned before in reference to FIGS. 2 and 3. An exemplary EKG signal EKGS, which represents a heart signal component or consecutive QRS complexes, is possibly present in an EMG signal. In this view, the signals are shown not absolutely scaled to the same size. An EMG signal EMSx is suppressed in such time windows, for which the heart signal component was detected. These time windows are indicated in detection information DIx on the basis of the values 0 and 1. The selection of the logical values 0 and 1 for the indication of the particular time window is only exemplary here, a reversed use of the values 1 and 0 is also possible. The signals EKGS, DIx, EMSx shown here shall only illustrate the basic principle of the detection step.

A heart signal component other than the QRS complex is the so-called p wave, which represents a possible disturbance as well. The p wave may be smaller than the QRS complex by a factor of 10.

A presence of an EKG signal or a QRS complex within the EMG signal can be detected by means of the so-called Pan-Tompkins algorithm Pan, Jiapu, Tompkins, Willis J., "*A Real-Time QRS Detection Algorithm,*" Biomedical Engineering, IEEE Transactions on, vol. BME-32, No. 3, pp. 230, 236, March 1985.

The Pan-Tompkins algorithm usually outputs a pulse stream. In this case, the temporal position of the QRS complex is marked by a single peak or spike. A preset temporal range or a time window around such a detected signal peak can be interpreted as the EKG signal or as the QRS complex, so that such a time window then represents one of the time windows with the value 0 of the detection information DIx. Such a time window preferably begins about 20 msec to 50 msec before the spike and ends 50 msec to 90 msec after the spike. The detection information DIx assumes the value 1 outside of the time window caused by a spike. For such detected time windows with the value 0, the EKG signal or the heart signal component is suppressed in the EMG signal EMSx. This suppression takes place by the EMG signal EMSx within these time windows being replaced by preset values, for example, zero values.

Figure 6:
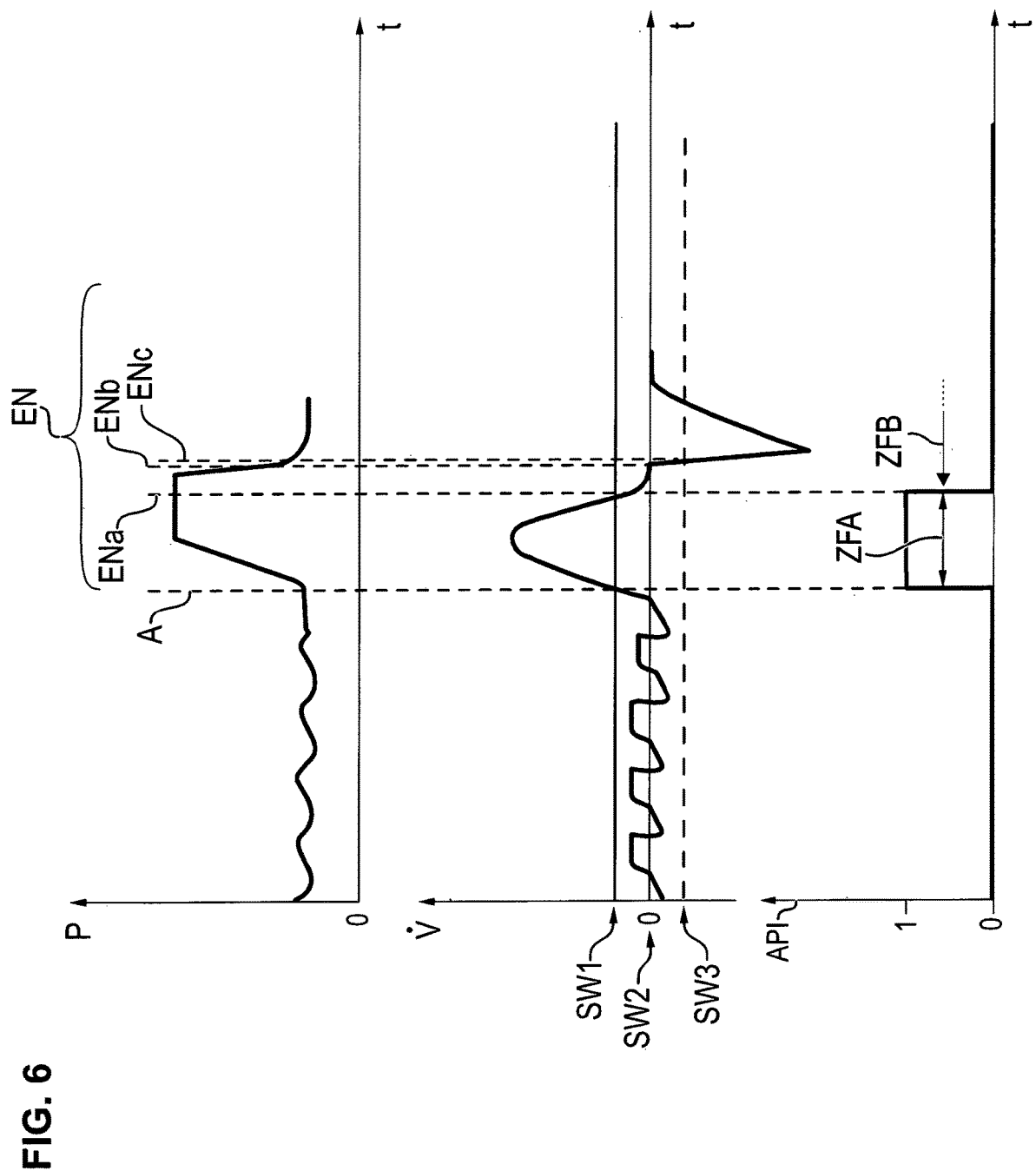
FIG. 6 is a graph view showing exemplary signals within the framework of obtaining breathing phase information together with a volume flow signal and with a pressure signal.

FIG. 6 shows exemplary signals within the framework of a determination step BS, which was mentioned before in reference to FIGS. 2 and 3. A volume flow signal $\dot{V}$, which represents, for example, an inspiratory phase and an expiratory phase, is shown over time t in FIG. 6. The breathing phase information API is determined on the basis of the breathing signal $\dot{V}$. The breathing phase information API indicates a first inspiratory time window ZFA of inspiratory breathing activity as well as a second expiratory time window ZFB of expiratory breathing activity. A time window of an inspiratory activity ZFA is defined here such that the inhalation by the patient essentially takes place during this time window ZFA. A time window of an expiratory activity ZFB is defined here such that the exhalation by the patient essentially takes place during this time window ZFB, but that the time window is not limited to such a partial period of the exhalation, but preferably comprises additional partial periods, preferably one additional partial period, which lasts up to a beginning of a next period or time window of a next inhalation.

If the breathing signal $\dot{V}$ exceeds a preset positive threshold value SW1, then the start time A of an inspiratory activity of the patient is implied. This time A may then be set as the beginning of the time window of the inspiratory activity ZFA. One of the end times ENa, ENb or ENc may preferably be used for the determination of an end time EN of the inspiratory breathing activity or of the beginning of the expiratory breathing activity, also called cycling off time. The particular end times ENa, ENb, Enc differ by particular, different threshold values SW1, SW2, SW3 being applied, which are fallen below by the volume flow signal $\dot{V}$ at the particular times. The beginning of the expiratory time window ZFB of the expiratory breathing activity is determined as the time EN1 by means of the threshold value SW1 in this example.

FIG. 6 further shows pressure values P which correspond to the volume flow $\dot{V}$ and which can be detected by means of a pneumatic sensor in the breathing circuit likewise or instead of the volume flow $\dot{V}$. An alternative determination of a start time A of an inspiratory phase or of an inspiratory time window is that the pressure signal P at the time A falls below a preset pressure threshold value. This is not so explicitly shown in FIG. 6. However, it may possibly be assumed that a so-called intake of breathing air in the breathing circuit by the patient in the course of an inspiratory breathing activity of the patient may lead for a short time to a drop in pressure, not shown here, below a preset threshold value, so that this time, at which this pressure threshold value is fallen below, can be determined as the start time A of the inspiratory breathing activity or of the time window of the inspiratory breathing activity. The determination of the end time of the inspiratory breathing activity or the beginning of an expiratory breathing activity may then be determined by referring to the volume flow signal as described before.

Figure 7:
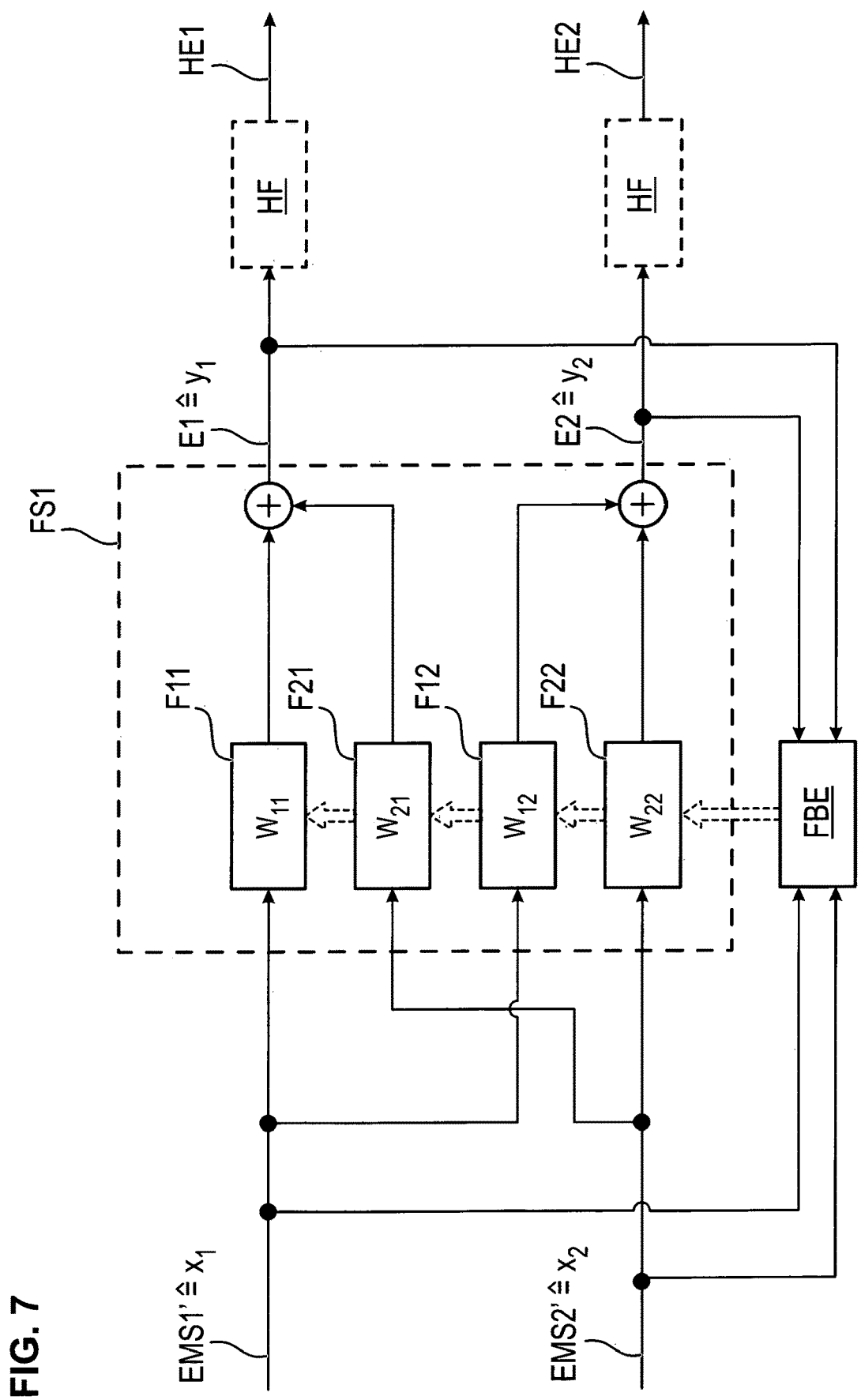
FIG. 7 is a schematic view showing steps for the determination of separated signals on the basis of EMG signals in the first exemplary embodiment.

FIG. 7 shows a signal processing step SV1 according to the first exemplary embodiment mentioned before in reference to FIG. 2. A digital signal processing or a digital filtering of the EMG signals EMS1', EMS2' is carried out on the basis of a digital filter structure FS1 in order to determine the separated signals E1, E2. The filter structure FS1 is a so-called matrix filter or matrix filter structure, in which each of the incoming signals EMS1', EMS2' may, in principle, contribute to a signal component of one of the outgoing signals E1, E2 or of the separated signals. The filters F11, ..., F22 are finite impulse response (FIR) filters here. These signal components are dependent on the filter coefficients of the individual filters F11, F21, F12, F22.

New, updated filter coefficients of the filters F11, F21, F12, F22 of the filter structure FS1, as well as current filter coefficients of the individual filters F11, ..., F22, are determined in an adaptive process in a step of the coefficient determination FBE with knowledge of the incoming EMG signals EMS1', EMS2', as well as of the outgoing, separated signals E1, E2.

The separation of the EMG signals EMS1', EMS2' preferably runs continuously over the incoming signals EMS1', EMS2'. The determination of the filter coefficients in the determination step FBE takes place in steps here. The determination of the filter coefficients of the individual filters F11, ..., F22 of the filter structure FS1 are determined here in a determination step FBE, which will be explained more precisely later.

The separated signals E1, E2 may preferably also be subjected to a Hull filtering HF. A different term for Hull filtering is envelope curve filtering. In this case, the particular separated signal E1, E2 is multiplied by a current rectangular window of about 30 msec and the so-called root mean square (RMS) value is subsequently calculated. A particular smoothed envelope curve signal HE1, HE2 is obtained due to a time shift of such a window and subsequent RMS value determination. Instead of a rectangular window, a window function may be selected here as well, which carries out a non-constant weighting of the individual signal values. This weighting may be, e.g., a trapezoid weighting. The weighting by means of the window function is preferably implemented as a finite impulse response filter.

Figure 8:
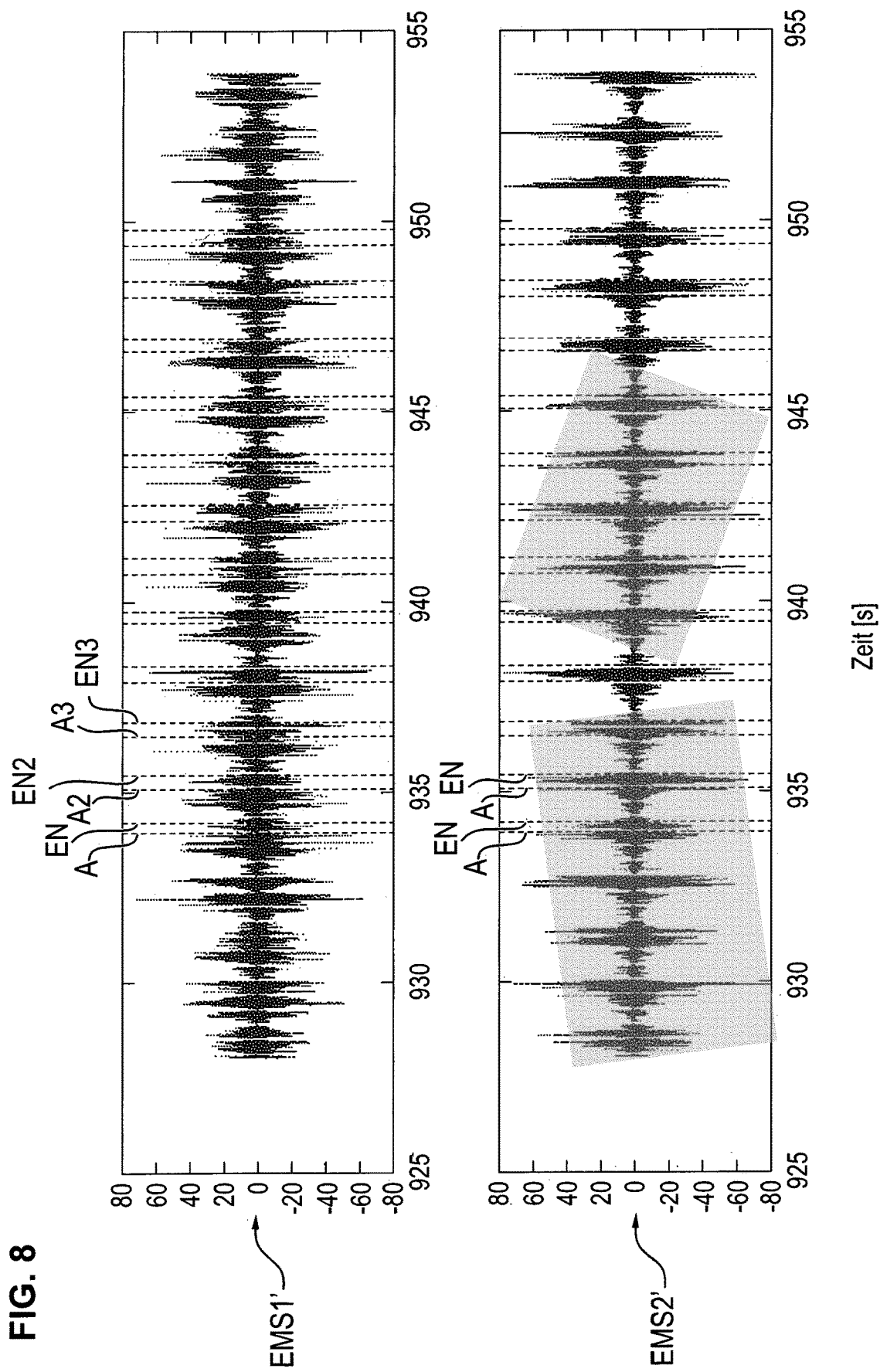
FIG. 8 is a graph view showing exemplary EMG signals before a separation according to the first exemplary embodiment.

FIG. 8 shows exemplary incoming EMG signals EMS1', EMS2' after removal of a possible EKG or heart signal component as was described before in reference to FIG. 2 and FIG. 5. FIG. 8 further shows start times A as well as end times EN of a time window of inspiratory activity, which indicate the breathing phase information, which was determined before on the basis of the breathing signal. The Hull-filtered signals HEEMS1' and HEEMS2' corresponding to the EMG signals shown from FIG. 8 are shown in FIG. 9 for a clearer view.

Figure 10:
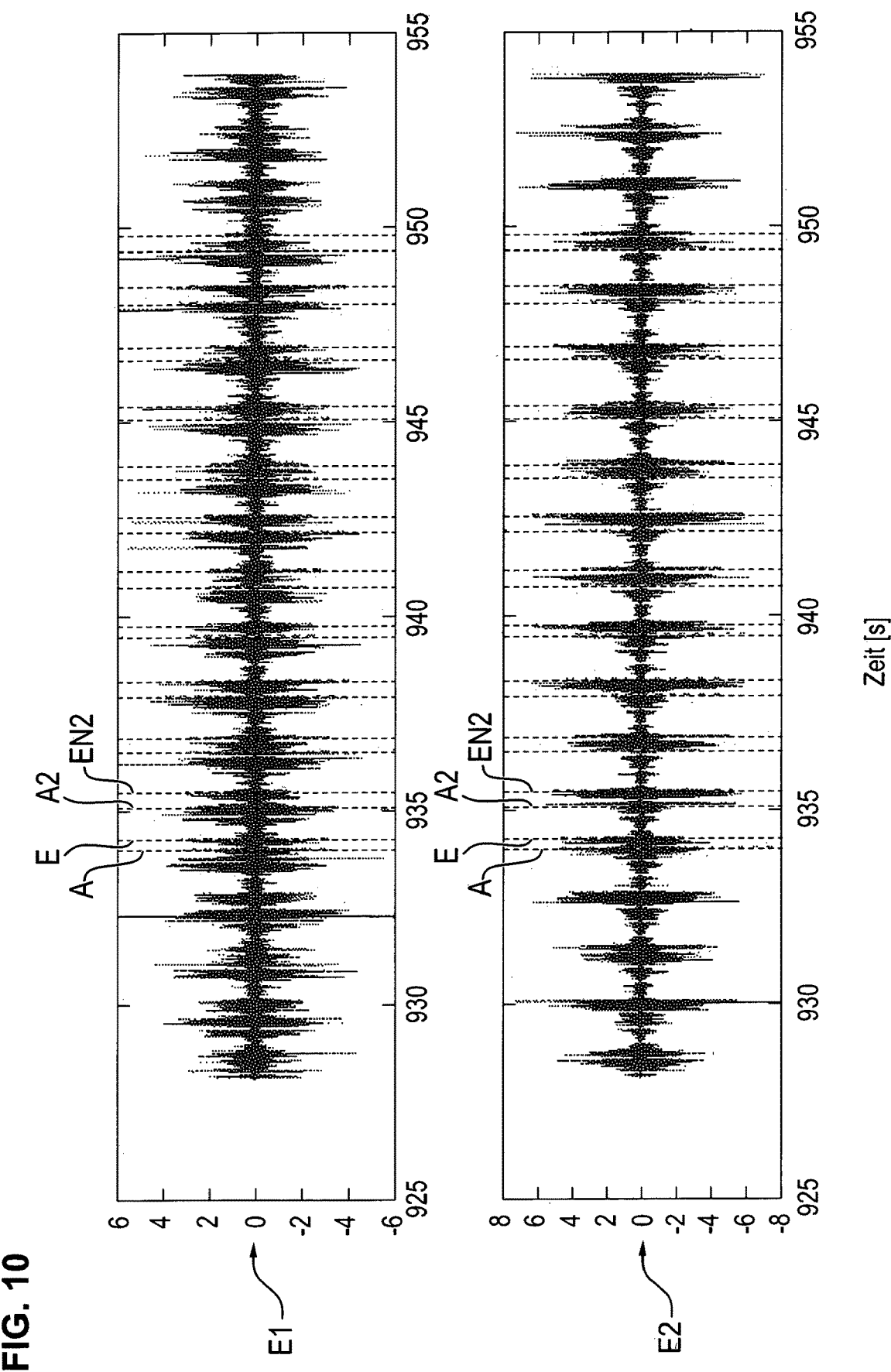
FIG. 10 is a graph view showing exemplary, separated signals according to the first exemplary embodiment.
Figure 11:
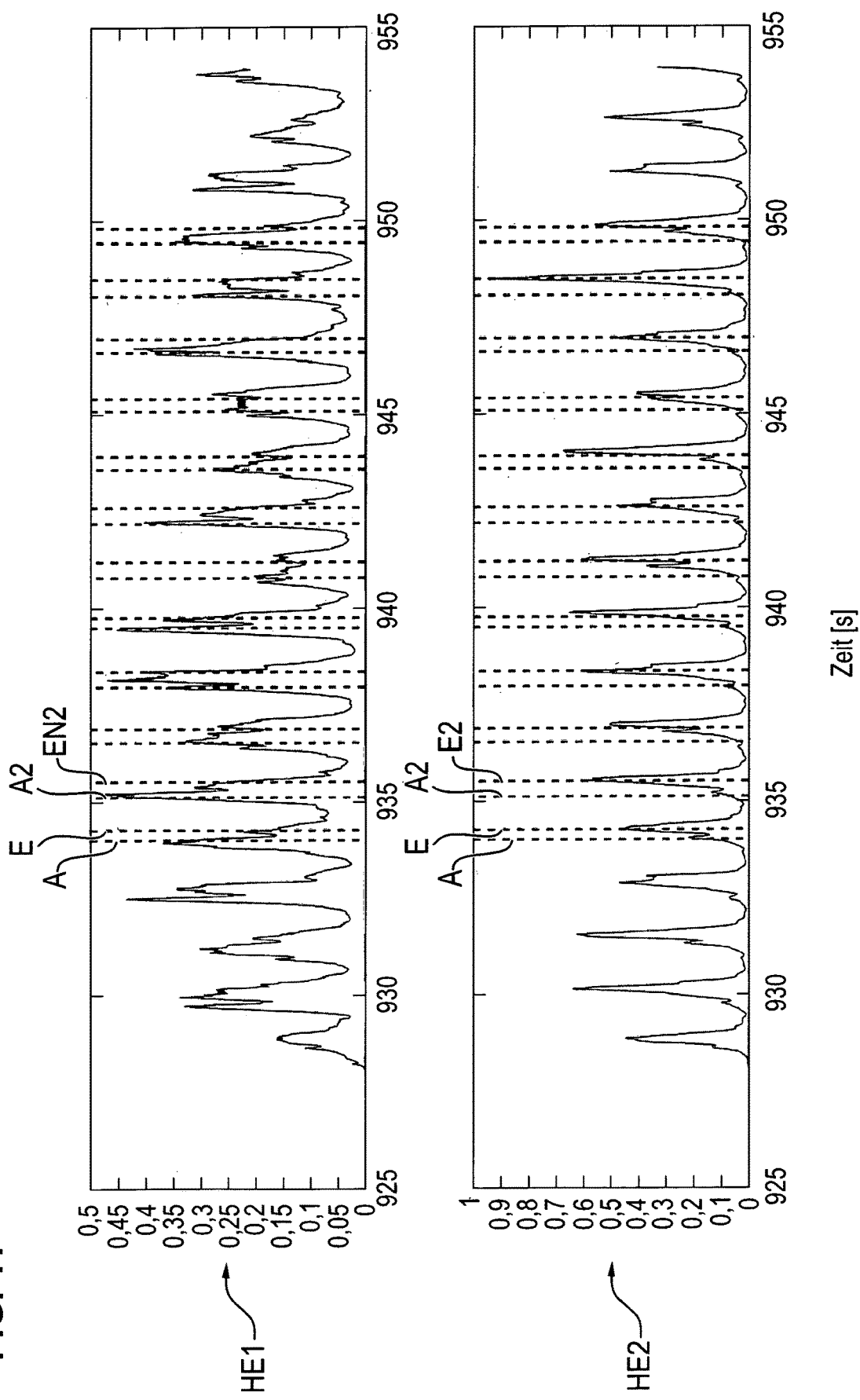
FIG. 11 is a graph view showing enveloping of the separated signals according to the first exemplary embodiment.

FIG. 10 shows exemplary separated signals E1, E2. FIG. 11 shows the corresponding, separated signals HE1, HE2, which were subjected to Hull filtering.

Figure 9:
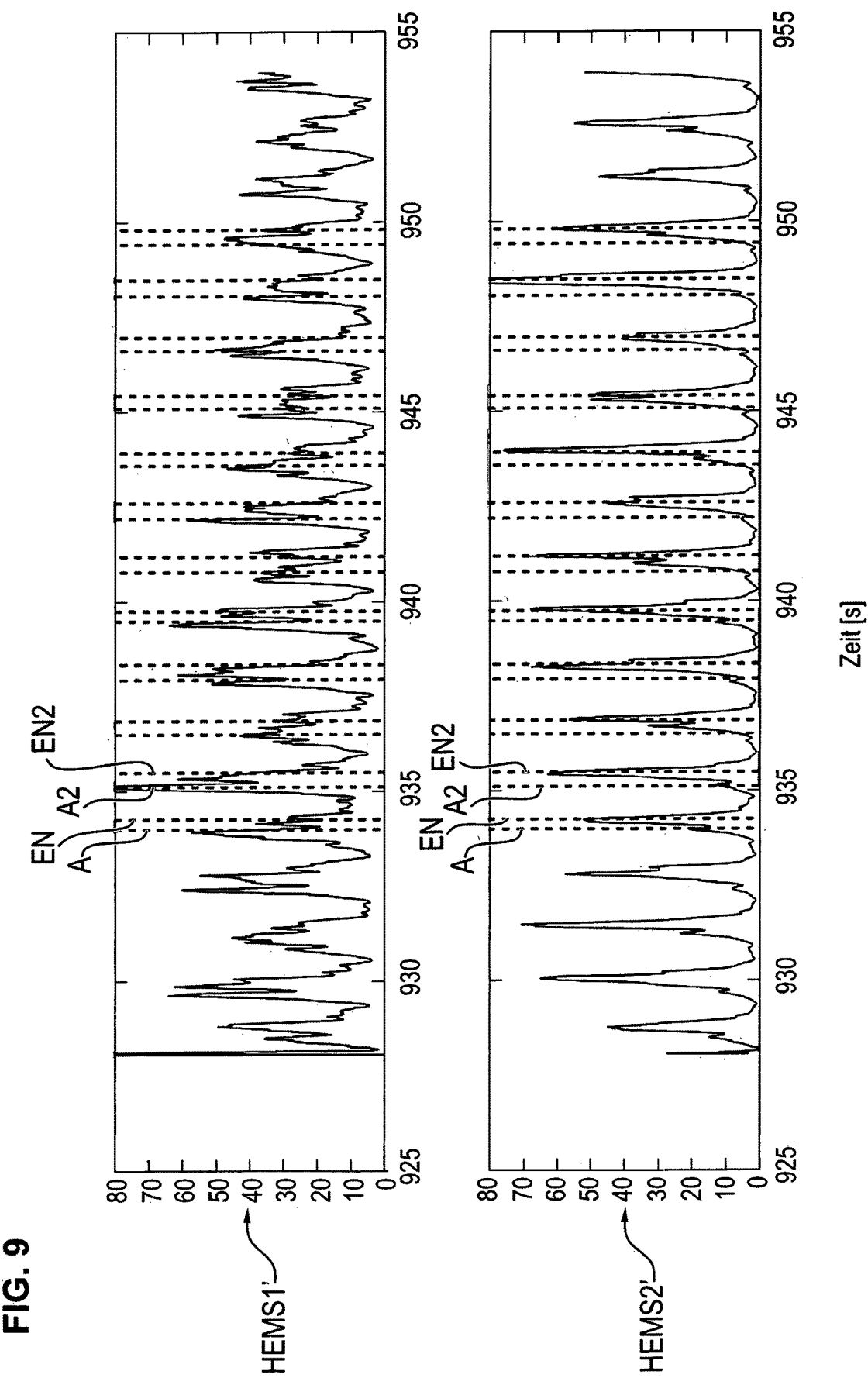
FIG. 9 is a graph view showing enveloping of the exemplary EMG signals before a separation according to the first exemplary embodiment.

In this case as well, the breathing phase information is shown in FIGS. 8, 9 and 10 and determined from the breathing signal plotted as start times and end times A, A2, EN, EN2 of inspiratory phases and inspiratory time windows.

By comparing the signals HEMS1', HEMS2' of FIG. 11 with the signals HE1, HE2 of FIG. 2, it can be seen that the signal HE1 from FIG. 11 represents a better representation of an inspiratory muscle activity than the signal HEEMS1' from FIG. 9, especially for the second inspiratory phase between the times A2 and EN2. In particular, the maximum peak between the points A2 and EN2 in the signal HE1 is clearly present within this time window, while this peak in the signal HEEMS1' also has a considerable component outside of this time window already before the time A2.

Figure 12:
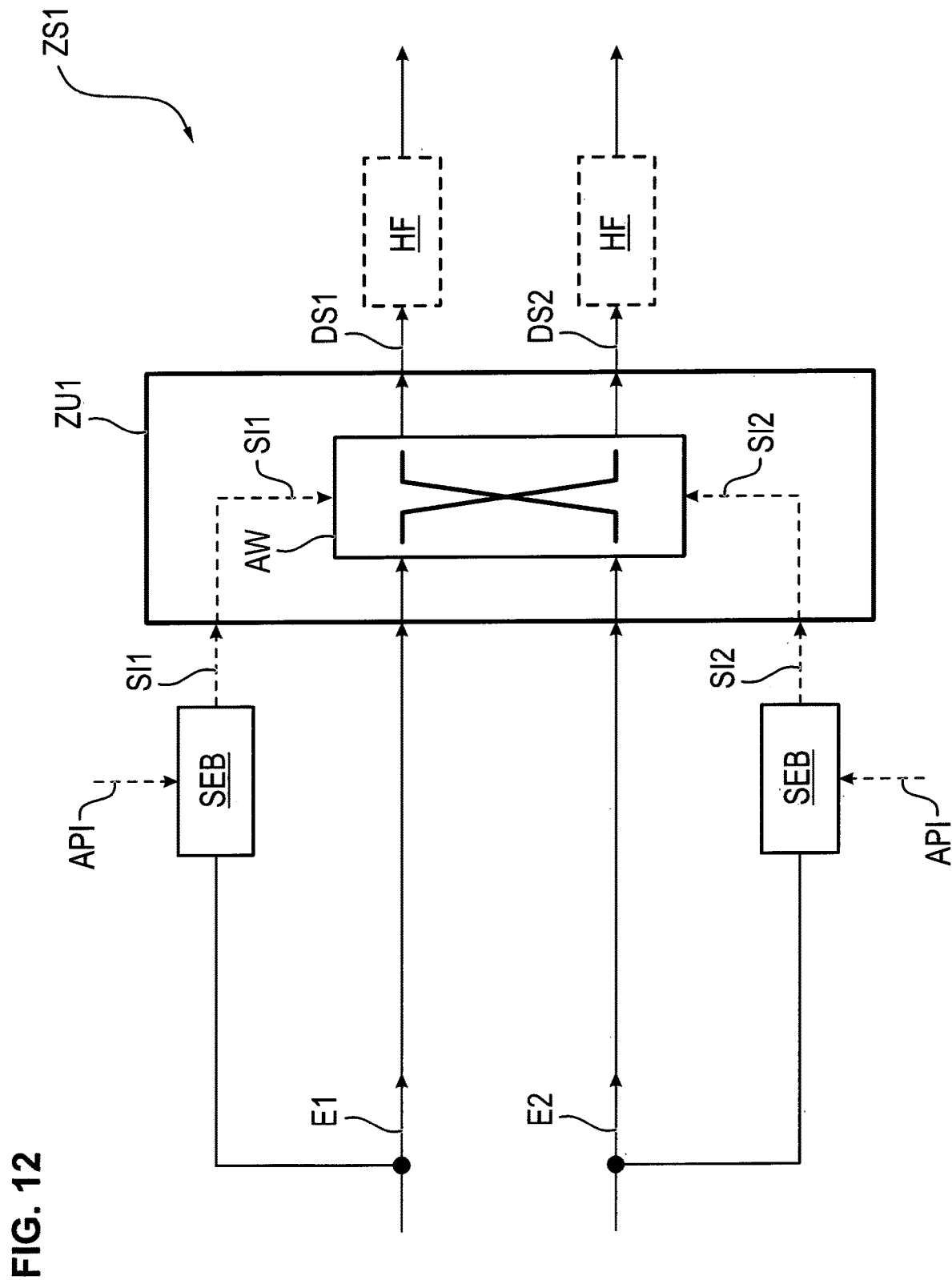
FIG. 12 is a schematic view showing steps for assigning separated signals for the purpose of the determination of the data signals as a function of the breathing phase information.

FIG. 12 shows partial steps of the above-mentioned assignment step ZS1, which was mentioned before in reference to FIG. 2 and in connection with the first exemplary embodiment.

The separated signals E1, E2 are first analyzed in a particular step of signal energy determination SEB with respect to their particular signal energy. Corresponding signal information SI1, SI2 is determined here with knowledge of the breathing phase information API obtained before. The step SEB is shown here as a step, which can be carried out separately for the signals E1 and E2, wherein it is obvious to the person skilled in the art that this step SEB is to be carried out with knowledge of both separated signals E1, E2, as will be explained later in reference to FIG. 13.

Figure 13:
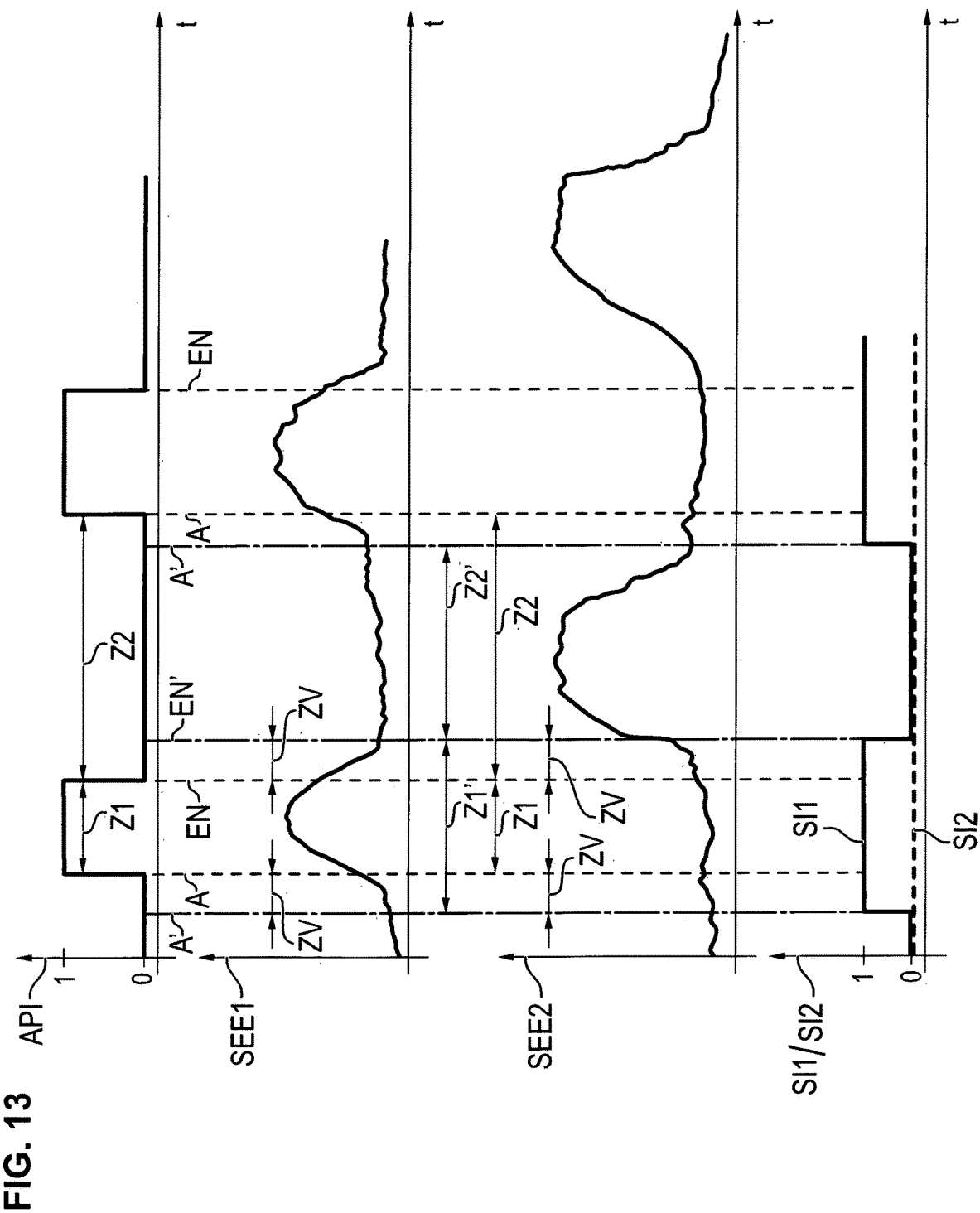
FIG. 13 is a schematic view showing exemplary signals within the framework of assigning the separated signals for the determination of the data signals.

FIG. 13 shows, as an example, breathing phase information API as well as an energy signal SEE1 obtained on the basis of the separated signal EN1 as well as an energy signal SEE2 obtained on the basis of the separated signal EN2. A basically assumed time window Z1 of an inspiratory activity, indicated by the breathing phase information API, is modified by particular time shifts ZV, which are preferably 100 msec, at its start A and at its end E. A modified time window Z1' with times A' and E' is thus obtained. This is thus a time window Z1', which can be assumed to be a time window of an inspiratory activity. The time window Z2 of the expiratory activity, which time window is indicated by the breathing phase information API, is modified according to the application of the time shift ZV in order to obtain the time window Z2'.

That signal of the separated signals E1, E2, for which the corresponding energy signal SEE1, SEE2 within the inspiratory time window Z1' has the higher or the highest signal energy, is determined as the signal for this time window Z1', which signal indicates an inspiratory muscle activity of an inspiratory breathing phase. In the example shown here, it is now thus assumed that the separated signal E1 indicates an inspiratory muscle activity during an inspiratory breathing activity of the patient, because the energy signal SEE1 has the highest signal energy within the time window Z1'. This is indicated in signal information SI1 on the basis of corresponding zero-one values, as is shown by a solid line in the lower signal curve SI1/SI2. Because the energy signal SEE2 has a lower signal energy during the inspiratory time window Z1' than the energy signal SEE2, this is indicated in signal information SI2, shown here as a dotted line, correspondingly by the value 0. The separated signal E2 may thus be assumed to be that signal, which indicates an expiratory muscle activity during an expiratory breathing activity of the patient, for the time window Z1'.

According to the view from FIG. 12, the signal information SI1, SI2 thus obtained can then be used in an assignment step ZU1 in the course of a selection step AW in order to assign the values of the separated signals E1, E2 to the data signals DS1 and DS2, respectively. In this case, that signal of the separated signals, here E1, is assigned to the first data signal D1, for which the highest number is obtained at time windows, at which the separated signal was assumed to be the inspiratory signal. The corresponding other signal, here E2, is assigned to the second data signal DS2. This is indicated and provided precisely by the signal information SI1, SI2, as explained in more detail before in reference to FIG. 13.

The derived data signals DS1, DS2 may preferably also be subjected to a Hull filtering HF.

Figure 14:
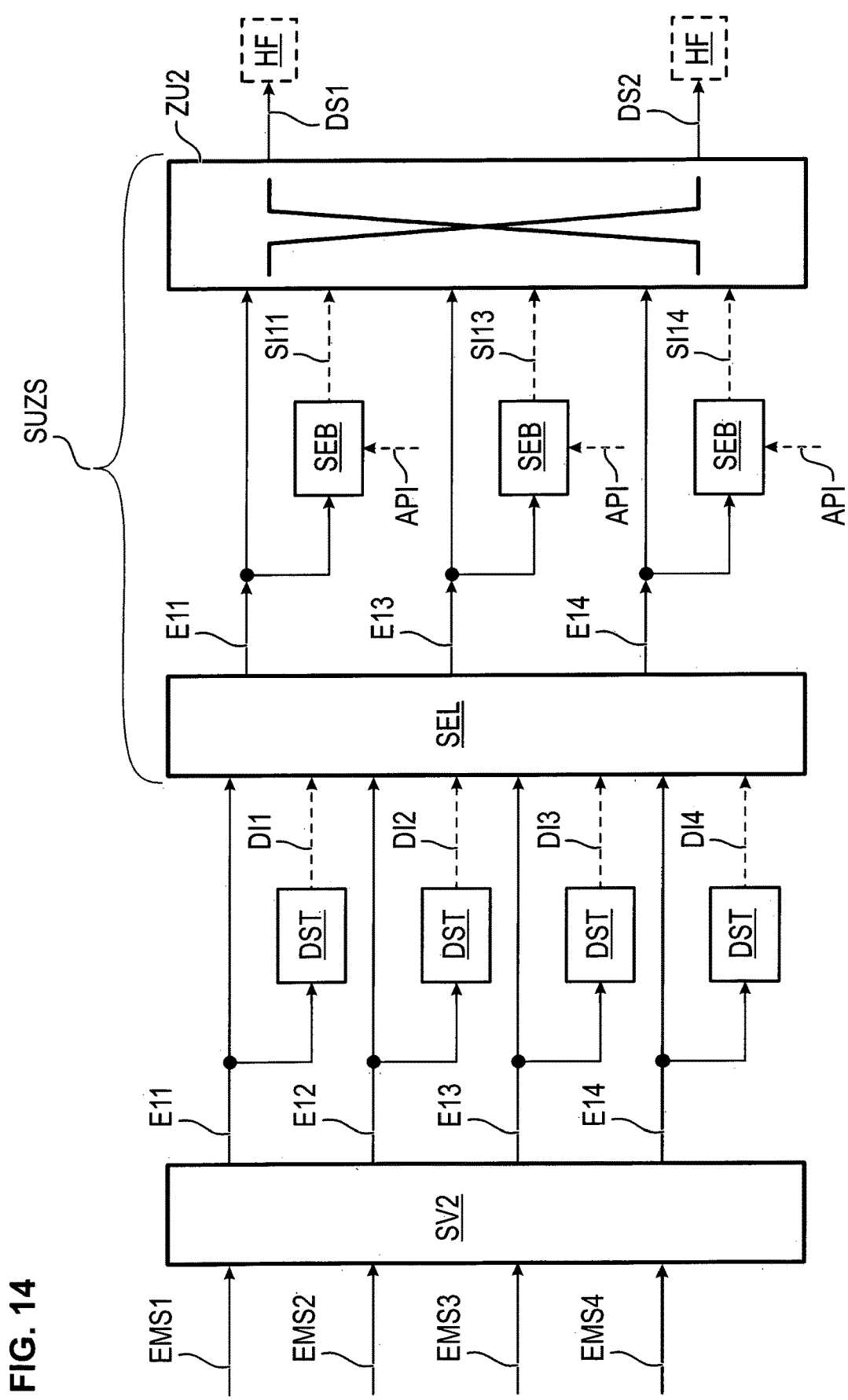
FIG. 14 is a schematic view showing a sequence of signal processing steps for the determination of the data signals on the basis of the EMG signals and of the breathing phase information according to the second exemplary embodiment.

FIG. 14 shows a determination of the data signals DS1, DS2 on the basis of at least three EMG signals, four EMG signals EMS1, . . . , EMS4 in this concrete example, as was explained before in reference to FIG. 3 according to the second exemplary embodiment. Here, the selection and assignment step SUZS is shown more precisely. The selection and assignment step SUZS consists of a selection step SEL and an assignment step ZU2.

On the basis of the detection information DI1, . . . , DI4 from particular detection steps DST, one of the four separated signals E11, . . . , E14 can be selected in the selection step SEL as the signal that most likely or essentially has a heart signal component or an EKG signal. Only three separated signals E11, . . . , E13 thus still remain. The selection of the separated signal E12 in the step SEL is only considered to be an example here, one of the other separated signals E11, E13, E14 could also be selected. That signal of the separated signals E11, E14 is selected on the basis of the detection information DI1, . . . , DI4 as the EKG signal or the heart signal, which has the most periods of time windows, within which a particular heart signal component could be detected.

The remaining, unselected, separated signals E11, E13, E14 are now each fed to a signal energy determination step SEB again, as was explained before under FIG. 13, wherein the breathing phase information API is used. Particular signal information SI11, SI13, SI14 is determined, as was explained before in reference to FIG. 13. On the basis of this signal information SI11, SI13, SI14, one of the signals E11, E13, E14 can then be identified or selected in the assignment step ZU2 as the signal, which indicates an inspiratory muscle activity. If two of the separated signals E11, E13, E14 compete with one another as inspiratory signals, then that signal, which indicates a higher breathing activity on the basis of a higher signal energy within the inspiratory phase, is assigned as the inspiratory signal to the first data signal DS1. The same statement can be made for a possibly competitive situation between two of the signals E11, E13, E14 with respect to an expiratory breathing activity during expiratory phases. Two of the signals E11, E13, E14, which were separated and not selected before in the step SEL, can thus be assigned in the assignment step ZU2 in order to obtain the data signals DS1, DS2. These signals DS1, DS2 may preferably again be subjected to a Hull filtering HF.

Figure 18:
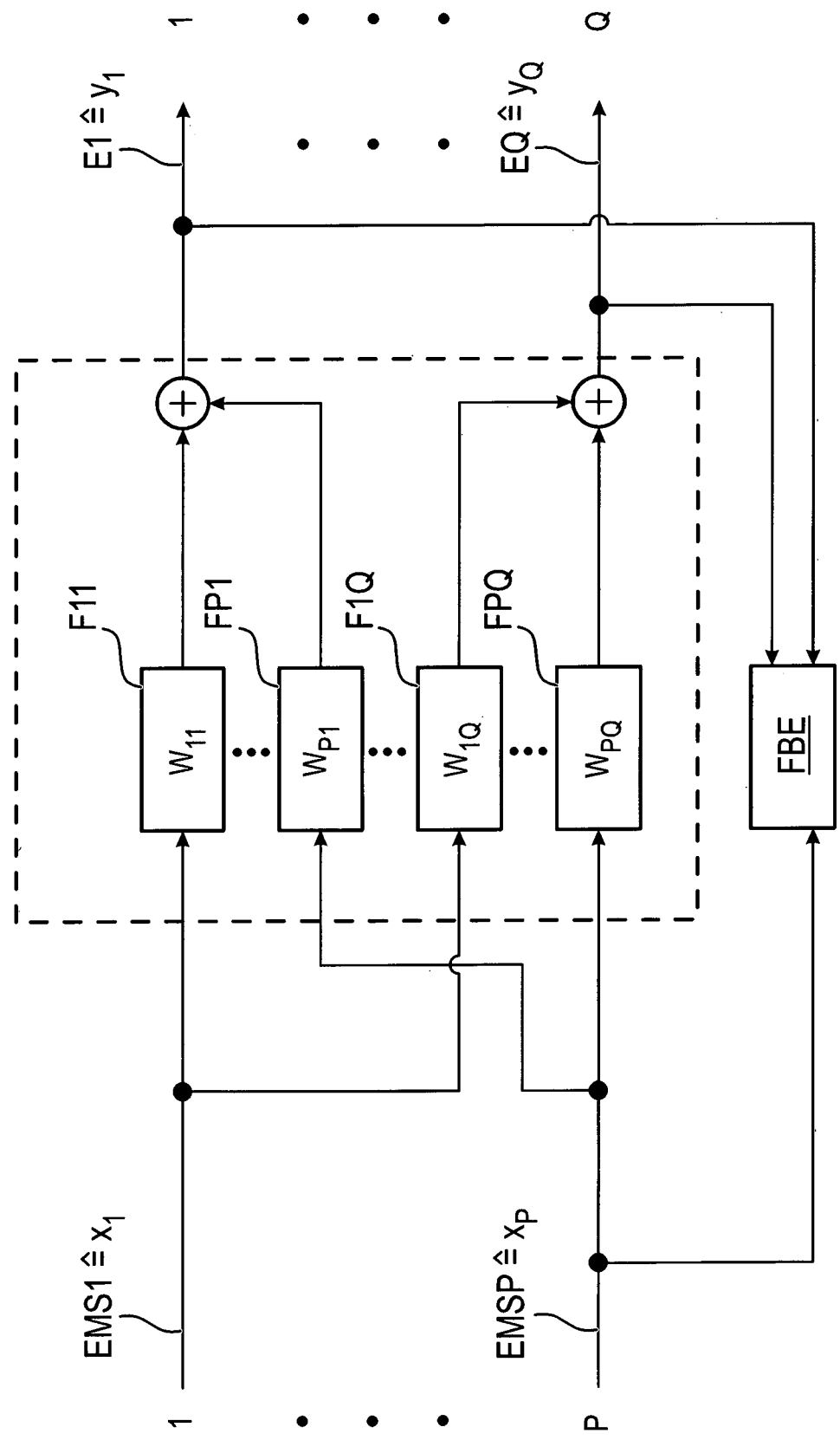
FIG. 18 is a schematic view showing a filter structure for the separation of the EMG signals for the purpose of the determination of the separated signals according to the second exemplary embodiment.

FIG. 18 shows a variant of the signal processing in the form of the signal processing step SV2, in which P different EMG signals EMS1, . . . , EMSP enter, here with P=4, and in which Q different output signals are determined as separated signals E1, . . . , EQ, here with Q=4. The filter structure FS2 is a matrix filter structure here, which shows the Q output signals from the P input signals. The filters F11, . . . , FPQ are FIR filters here. The filter coefficients of the individual filters F11, . . . , FPQ of the filter structure FS2 are in turn determined in a determination step FBE here, wherein new, updated filter coefficients of the filters, as well as current filter coefficients of the individual filters, are determined in an adaptive process with knowledge of the incoming EMG signals EMS1, . . . , EMSP as well as of the outgoing, separated signals E1, . . . , EQ.

It is now explained in reference to the second exemplary embodiment and FIG. 18 how filtering of the incoming EMG signals EMS1, . . . , EMSP can take place for obtaining the separated signals E1, . . . , EQ. In this case, it is clear to the person skilled in the art that the selection of P=4 and Q=4 is only one possible selection; P=2 and Q=2 signals may also be used, as was mentioned before in reference to the first exemplary embodiment.

The P present EMG signals EMS1, . . . , EMSP are time-discrete signals. I samples each of a signal EMS1, . . . , EMSP are used for determination of the filter coefficients, wherein the corresponding signal segments are cut out of the signals EMS1, . . . , EMSP at the same time. A corresponding signal $x'_p(i)$ is thus obtained for a signal EMSp with the channel index p=1 . . . P of the P channels in a sample index I=1 . . . I, as indicated by the signals $x'_1(i)$ and $x'_p(i)$ in FIG. 18. A vector, which has the individual values of the individual P channels for a time or sample index i is then given as $$x'(i)=[x'_1(i), \ldots, x'_P(i)]^T.$$

For the purpose of a so-called Sphering, a principal component analysis or eigenvalue decomposition of the spatial covariance matrix is first carried out by means of $$E\,D\,E^T = \hat{E}\{x'(i)x'^T(i)\},$$

so that the Sphering can then be carried out by means of $$x(i) \leftarrow E\,D^{-1/2}E^T x'(i).$$

The thus obtained signals $x_p(i)$ may then be split into M signal blocks of particular block length N with the block index m=1 . . . M, wherein blocks following one another overlap up to 50%, wherein the number of blocks is then $$M = \frac{I}{\frac{N}{2}}.$$

There are then n+1 N samples within one signal block.

A signal block with the index m and current sample index n=1 . . . N is then given by $x_p(m,n)=x_p(n+(m-1)*N/2)$. A frequency transformation, preferably a Fast Fourier Transformation (FFT), is then carried out for each of the channels with index p=1 . . . P and each block $$X_p^{(r)}(m)=\text{FFT}\{x_p(m,n)\},$$

wherein r is the frequency index of the L discrete frequency bins r=1 . . . L. For a fixed block index m and a fixed frequency index r, a vector of the dimensionality 1× P is then obtained for the frequency-transformed value $X_p^{(r)}(m)$.

Further, a so-called centering of the frequency-transformed value takes place according to $$X_p^{(r)}(m) \leftarrow X_p^{(r)} - \frac{1}{N}\sum_{m'=0}^{N-1} X_p^{(r)}(m').$$

On the basis of the now present frequency-transformed value $X_p^{(r)}(m)$, filter coefficients can then be calculated in the frequency range for the filters F11, . . . , FP1. This takes place iteratively over a preset number of $l_{max}$ iterations, wherein l=1 . . . $l_{max}$ is the iteration index.

The Q output signals and the Q separated signals E1, . . . , EQ with channel index q=1 . . . Q in the time range are assumed here to be $y_q(I)$ which can then be written as $$Y^{(r)}(m)$$

in the frequency range in the course of the block processing.

The frequency response of a filter Fpq from FIG. 18 with the filter index p, q can be written in the frequency range as $W_{pq}^{(r)}$ with the frequency index r=1 . . . L. The entire transfer function of the entire filter structure from FIG. 18 can then be written as $$W^{(r)l} = \begin{bmatrix} W_{11}^{(r)} W_{12}^{(r)} & \ldots & W_{1P}^{(r)} \\ \vdots & \ddots & \vdots \\ W_{Q1}^{(r)} & \ldots & W_{QP}^{(r)} \end{bmatrix}$$

for the current iteration l. For the first iteration l=1, initialization values $W^{(r)l-1}$ can be used for the transfer functions and first output signals $Y^{(r)}(m)$ in the frequency range can then thus be determined in this first iteration l=1 according to $$Y^{(r)}(m)=W^{(r)l-1}X^{(r)}(m)$$

wherein $$X^{(r)}(m)=[X_1^{(r)}(m), \ldots, X_P^{(r)}(m)]^T,$$

$$Y^{(r)}(m)=[Y_1^{(r)}(m), \ldots, Y_P^{(r)}(m)]^T.$$

A broad-band standardization factor $$b_p(m) = \sqrt{\frac{1}{M}\sum_{r=0}^{m-1}|Y_p^{(r)}(m)|^2}$$

can then be determined per channel p=1 ... P and block m= 1 ... M. A standardized multivariate score function can now be established according to $$\Phi^{(r)}(m) = \left[\frac{Y_1^{(r)}(m)}{b_1(m)}, \ldots, \frac{Y_p^{(r)}(m)}{b_p(m)}\right]^T.$$

New filter coefficients in the time range for the current iteration l can then be determined in an update step on the basis of the previous iteration l−1 according to $$W^{(r)l} = W^{(r)l-1} + \mu\left[I - \frac{1}{N}\sum_{m=0}^{N-1}\Phi^{(r)}(m)(Y^{(r)}(m))^H\right]W^{(r)l-1}$$

Here, μ is an increment factor from the range 0<μ<1.

The filter coefficients $W^{(r)l}$ may preferably still be subjected to a minimum distortion principle $$W^{(r)l} \leftarrow \text{diag}\{(W^{(r)l})^{-1}\}W^{(r)l}.$$

For carrying out another iteration l+1, it is now possible to begin again with the above step of the determination of the output signals of the output signals $Y^{(r)}(m)$ in the frequency range determined on the basis of the new filter coefficients $W^{(r)l}$ according to $$Y^{(r)}(m) = W^{(r)l}X^{(r)}(m)$$

Thus, $l_{max}$ iterations are then carried out, which lead to filter coefficients $$W^{(r)l\_max} = \begin{bmatrix} W_{11}^{(r)}W_{12}^{(r)} & \cdots & W_{1P}^{(r)} \\ \vdots & \ddots & \vdots \\ W_{Q1}^{(r)} & \cdots & W_{QP}^{(r)} \end{bmatrix}.$$

Frequency Values $$W_{pq} = [W_{pq}^{(r=1)} \ldots W_{pq}^{(r=L)}]$$

are now thus given for a filter from FIG. 18 with the index pq. Filter coefficients $w_{p,q}$ with coefficient index k and filter length K in the time range $$w_{p,q} = [w_{p,q}(k=1) \ldots w_{p,q}(k=K)]$$

can then be determined for this filter with the index pq by an inverse transformation according to $$w_{p,q} = \text{IFFT}\{W_{p,q}\}.$$

By applying the filter coefficients to the FIR filters F11, ..., FPQ, the input signals EMS1, ..., EMSP can then be filtered in order to obtain the separated signals E1, ..., EQ.

The above-described determination of the filter coefficients preferably takes place in steps such that first signal segments of the input signals EMS1, ..., EMSP are used for the determination of the first filter coefficients, that these first filter coefficients are then first continually applied to the additional input signals EMS1, ..., EMSP incoming over time, and that the filter coefficients are then adapted to additional, later times according to the above-described algorithm.

Alternative embodiments of algorithms for the separation of input signals and for obtaining of output signals are found in the following sources, among others:

H. Buchner, R. Aichner, and W. Kellermann, "*Blind source separation for convolutive mixtures: A unified treatment,*" In Y. Huang and J. Benesty (eds.), *Audio Signal Processing for Next-Generation Multimedia Communication Systems*, Kluwer Academic Publishers, Boston/Dordrecht/London, pp. 255-293, February 2004;

H. Buchner, R. Aichner, and W. Kellermann, "*TRINICON-based blind system identification with application to multiple-source localization and separation,*" In S. Makino, T.-W. Lee, and S. Sawada (eds.), *Blind Speech Separation*, Springer-Verlag, Berlin/Heidelberg, pp. 101-147, September 2007; and H. Buchner, R. Aichner, and W. Kellermann, "*A Generalization of Blind Source Separation Algorithms for Convolutive Mixtures Based on Second Order Statistics,*" *IEEE Transactions on Speech and Audio Processing*, Vol. 13, No. 1, pp. 120-134, January 2005.

Figure 15:
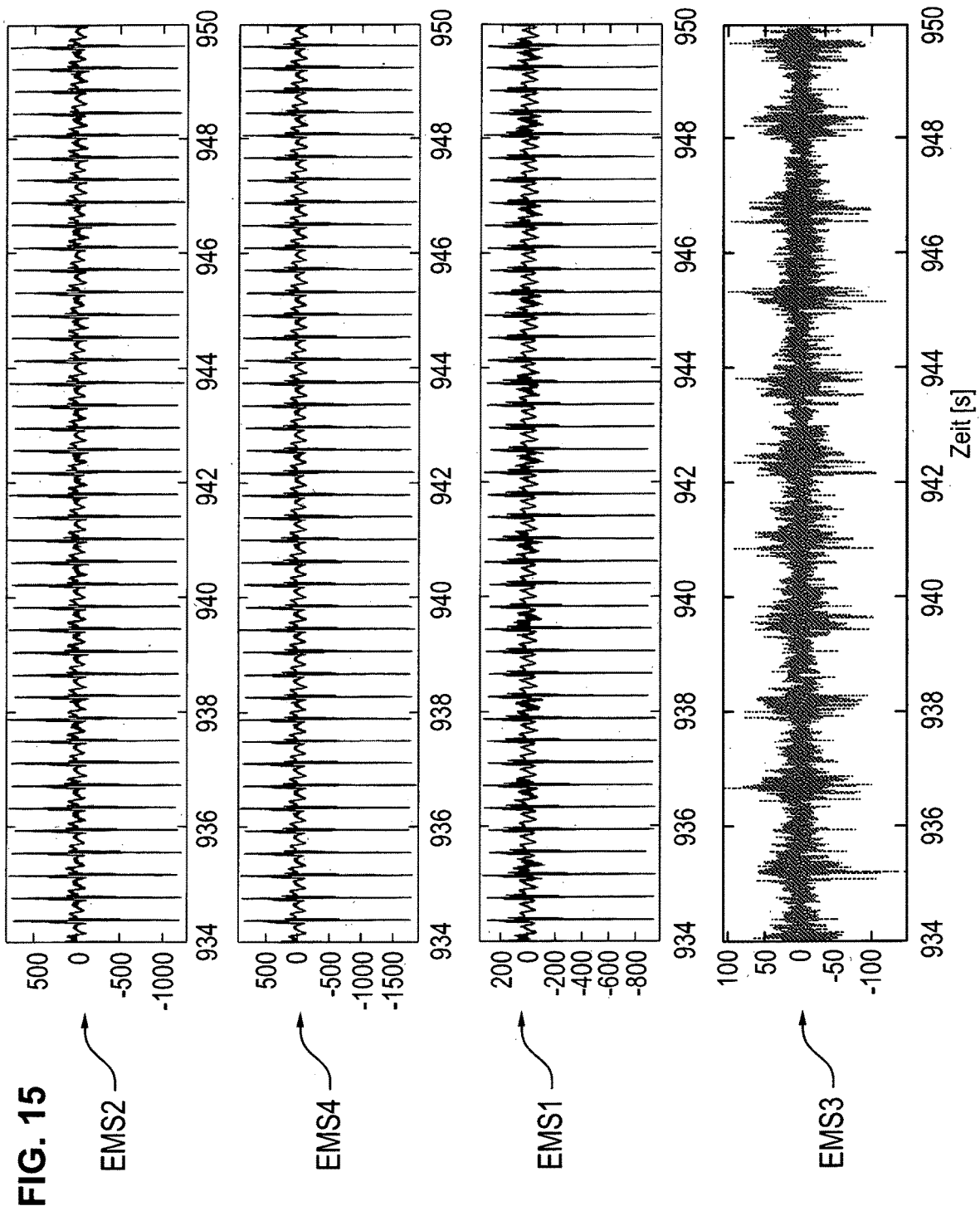
FIG. 15 is a graph view showing exemplary EMG signals according to the second exemplary embodiment.

FIG. 15 shows exemplary signals corresponding to those signals that are mentioned in reference to FIG. 14. Here, the EMG signal EMS2 represents that signal, which was obtained at the lower diaphragm, the signal EMS4 represents that signal, which was obtained at the upper diaphragm, the signal EMS1 represents that signal, which was obtained at the internal intercostal muscle, and the signal EMS3 represents that signal, which was obtained at the sternum. These signals are freed from their respective DC component by means of high-pass filtering.

Figure 16:
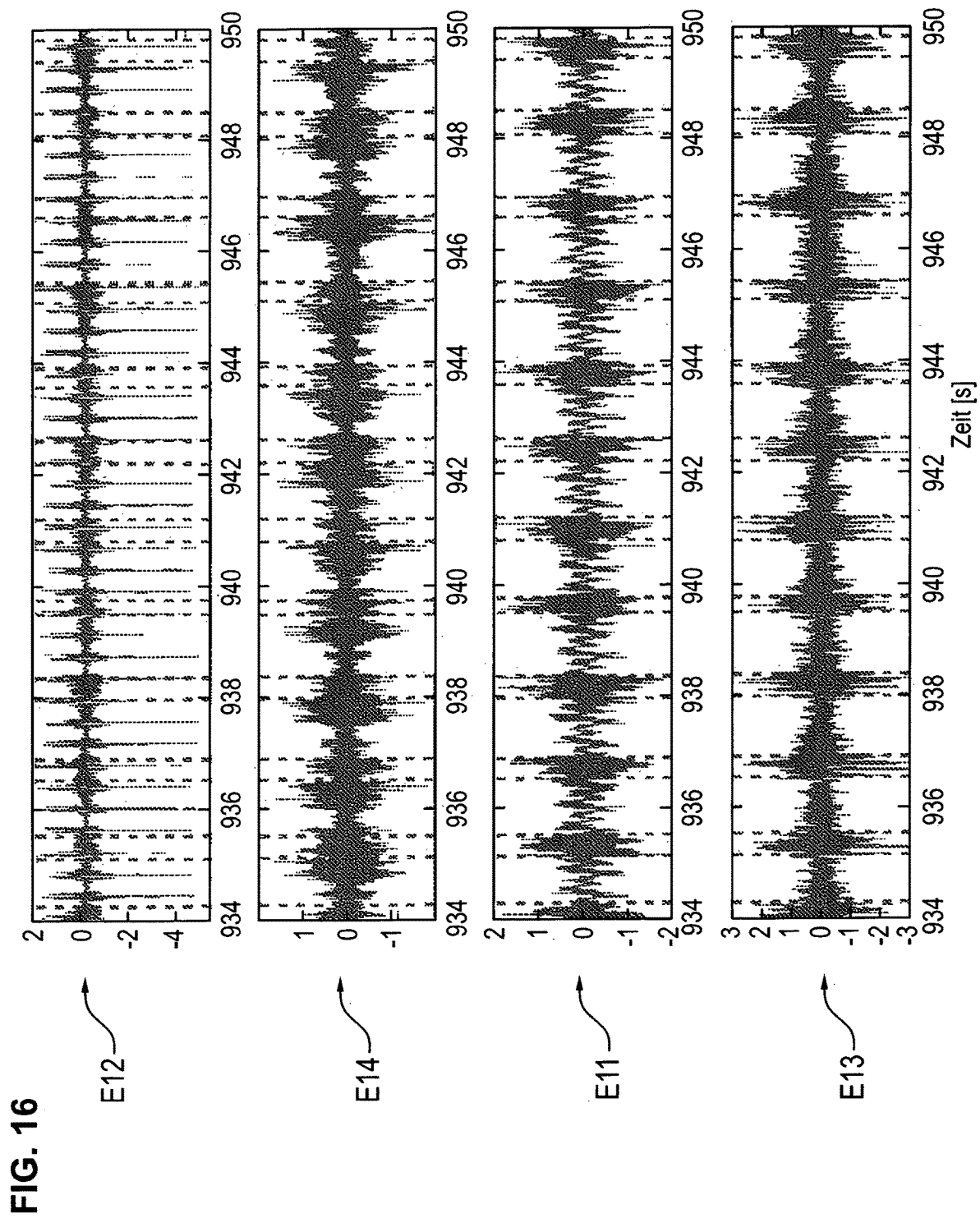
FIG. 16 is a graph view showing exemplary, separated signals according to the second exemplary embodiment.

FIG. 16 shows, as an example, separated signals E11, ..., E14, which result from a separation of the EMG signals from FIG. 15.

Figure 17:
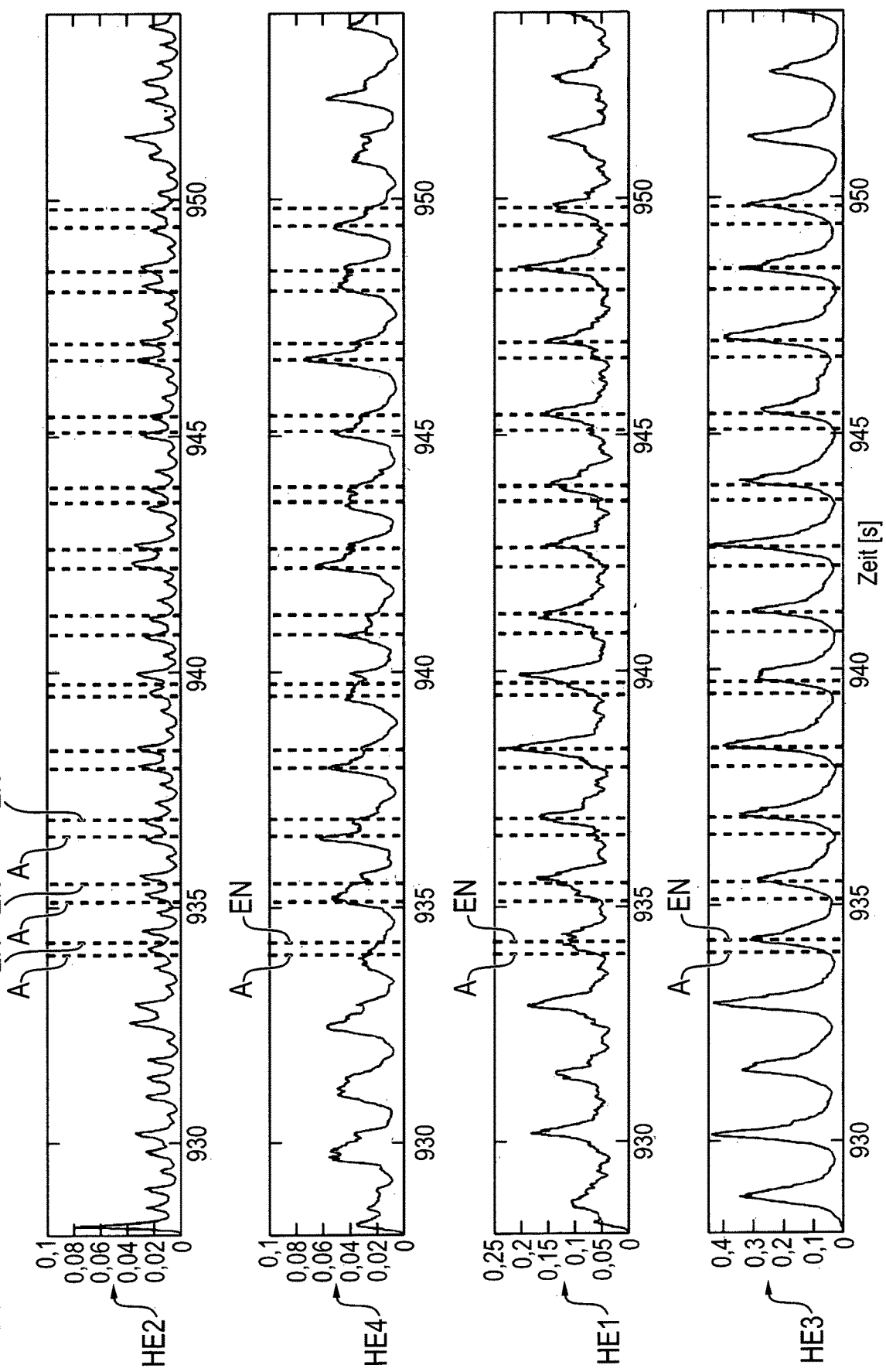
FIG. 17 is a graph view showing enveloping of the separated signals according to the second exemplary embodiment.

FIG. 17 shows the separated signals from FIG. 16 after Hull filtering, as was already mentioned in reference to FIG. 14. In FIG. 17, the corresponding filtered signal HE2 is in this case mainly that signal, which has an EKG signal component, whereas the other signals HE4, HE1, HE3 each indicate an inspiratory or an expiratory muscle activity of the patient.

The respective start times and end times A, EN of the individual time windows of inspiratory or expiratory activity are in turn shown in FIG. 17. It can be seen here that, for example, just the signal HE4 or even the corresponding signal E14 indicates a muscle activity of inspiratory activity.

It is further seen that a heart signal component is contained in an extremely dominant manner in each of the incoming EMG signals EMS2, EMS4, EMS1 from FIG. 15, that, however, because of the separation and filtering for the determination of the separated signals E12, E14, E11, E13, see FIG. 16, the respective EKG signal component or the cross-talk of the EKG signal into the signals EMS4 and EMS1 could be markedly reduced. The process shown here thus appears to be capable of carrying out separation of EMG signals with respective cross-talk components in order to obtain signals which indicate an inspiratory or expiratory muscle activity. This process is hence especially efficient, because the breathing phase information API, which is obtained from the breathing signal, is effective as reference information.

FIG. 19a shows a preferred exemplary embodiment of the device V according to the present invention, in which the data signals DS1, DS2 determined by the computer R are each subjected to a Hull filtering HF, before display data AD, which indicate the data signals DS1, DS2, are provided via an external display interface or display interface DIS. The display data AD may then be displayed on a display unit not shown here in order to display to the clinician information about the presence of an inspiratory or expiratory muscle activity. Therefore, the Hull filtering is shown here in dotted line, because this is to be carried out optionally or only if preferred.

The display data AD can be structured such that a diagram of the signals DS1, DS2 can be made as a time series, wherein an inspiratory activity is plotted as positive and an expiratory activity is plotted as negative.

The display data AD are preferably structured such that a diagram is made as a pictogram, wherein the electrode positions can be displayed together with the result of the assigned, separated source signals, so that corresponding muscles can be shown in terms of their activity.

The display data AD can preferably, in addition, have or indicate the EKG signal selected within the framework of the selection.

FIG. 19b shows a variant of the device V, in which an external data interface EDS provides an output data signal DAS, which indicates the data signals DS1, DS2. In this case, the data signals DS1, DS2 are also subjected to a Hull filtering HF, before these data signals are forwarded to the external data interface EDS. The output data signal DAS is suitable here for transmission by the external data interface EDS via a communication medium, for example, a network. The network may be a wireless network or a wired network.

Figure 20:
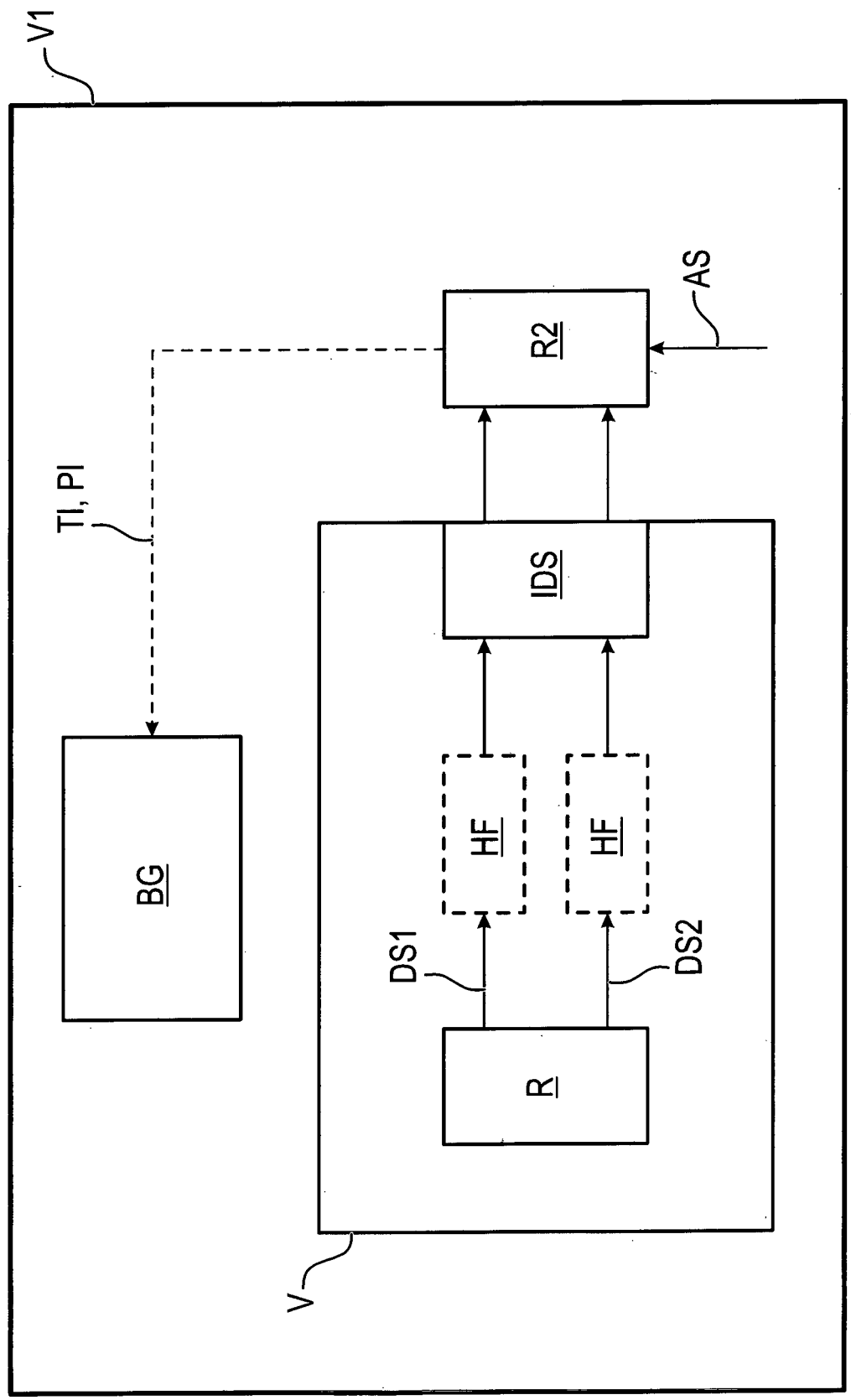
FIG. 20 is a schematic view showing an advantageous embodiment of the device according to the present invention comprising the ventilator.

FIG. 20 shows a preferred embodiment V1 of the device, in which the obtained data signals DS1, DS2 are subjected to a Hull filtering, only if preferred, and are then forwarded via an internal data interface IDS to another computer R2 of the device V1. The device V1 comprises the ventilator BG. The above-mentioned at least one computer is a combination of the computers R and R2 here.

The computer R2 is configured to receive the breathing signal AS. The computer R2 is further suitable to actuate the ventilator BG as a function of at least one of the data signals DS1, DS2. For this, the computer R2 provides trigger information TI with knowledge of the data signals DS1, DS2 to the ventilator BG. As a result, the ventilator BG can use this trigger information TI to trigger the ventilation of the patient within the framework of a ventilation mode.

Figure 21A:
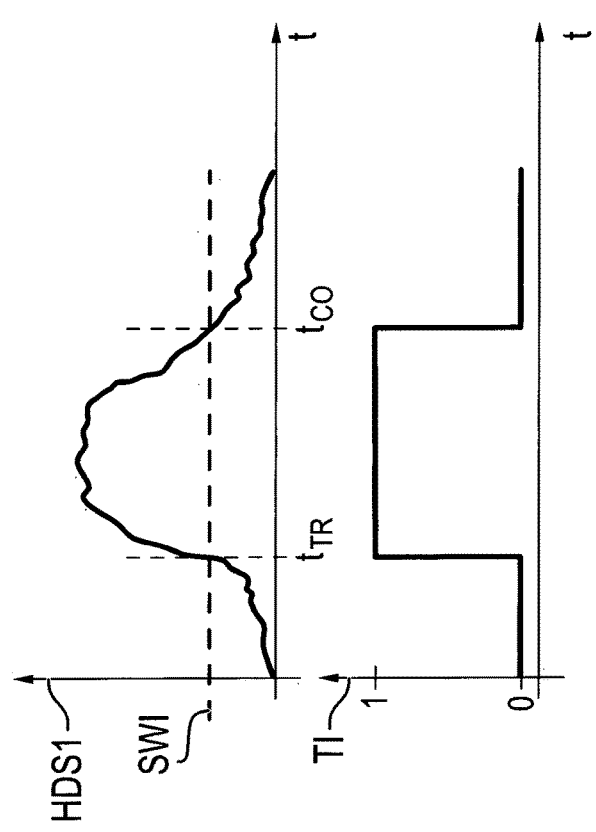
FIG. 21a is a graph view showing exemplary signals for obtaining actuation information or trigger information for the purpose of the actuation of a ventilator on the basis of at least one data signal.

FIG. 21a shows exemplary signal curves for obtaining the trigger information TI. The signal DS1 filtered with a Hull filter, shown here as HDS1, is plotted over time t. If the Hull-filtered data signal HSD1 exceeds a preset threshold value SWI, a time tTR is set, at which a triggering or beginning of an inspiratory phase begins. This is indicated by the trigger information TI jumping, for example, from the value 0 to the value 1.

The end of the inspiratory phase or the time of the so-called cycling off is present if the Hull-filtered data signal HDS1 falls below the preset threshold value SWI, so that it may be indicative of the time $t_{CO}$. The trigger information TI is again correspondingly changed from the value 1 to the value 0.

Figure 21B:
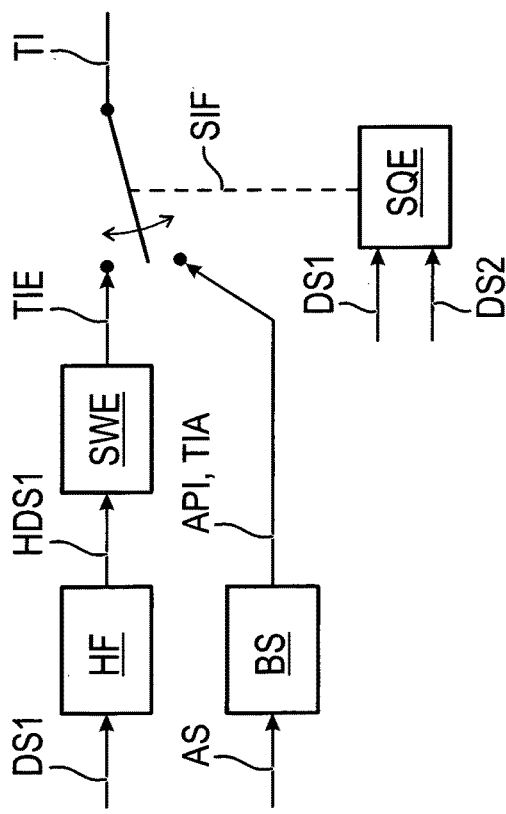
FIG. 21b is a schematic view showing steps for the quality evaluation of at least one of the data signals in order to use either at least one of the data signals or the breathing signal for the actuation of the ventilator as a function of the quality evaluation.

FIG. 21b shows a block diagram of an evaluation and signal processing, in which the computer R2 as part of the at least one computer is configured to actuate the ventilator BG both as a function of the at least one data signal DS1 and as a function of the breathing signal AS. The computer R2 is further configured to carry out a quality evaluation of the data signal DS1 within the framework of an evaluation step SQE. Further, the quality evaluation SQE is preferably also carried out on the basis of the data signal DS2. The result of the quality evaluation is switching information SIF. The computer R2 is configured to use either the one data signal DS1 directly or indirectly to actuate the ventilator BG at times as a function of the quality evaluation carried out in the step SQE or of the switching information SIF, or else at times to use the breathing signal AS without the data signal DS1 to actuate the ventilator BG. This takes place on the basis of the quality evaluation SQE carried out. The trigger information TI is thus determined on the basis of the one data signal DS1 or of the breathing signal AS.

The breathing signal AS is analyzed in a determination step BS, so that breathing phase information API is obtained. This determination step BS was described more precisely in detail before in reference to FIG. 6. The breathing phase information API indicates times of a trigger or the beginning of an inspiratory phase and an end of an expiratory phase, which is called a cycling off time.

The above-mentioned Hull filtering HF of the first data signal DS1 for obtaining the Hull-filtered data signal HDS1 takes place in an upper branch of FIG. 21b. In a threshold value decision step SWE, as explained before more precisely in reference to FIG. 21a, the trigger information TIE is then obtained, which is identical to the trigger information TI from FIG. 21a. This is thus trigger information TI, which is obtained on the basis of the EMG signal or the plurality of EMG signals. The breathing phase information API may also be regarded as breathing trigger information TIA. In the quality evaluation step SQE is thus obtained information SIF, which decides whether the trigger information TI obtained before on the basis of the EMG signals is outputted as trigger information TI or else the trigger information TIA obtained on the basis of the breathing signal AS is outputted. This is then the final trigger information TI, which is likewise shown in FIG. 20.

Within the framework of the quality evaluation step SQE, this switching information SIF is obtained such that if an EMG-based trigger signal TIE, which is qualitatively not of high quality, is present, the inspiratory signal AS is used to obtain the trigger information TIA. The signal quality information SIF, also called signal quality index, can be determined, for example, in such a way that the particular signal energy can be set into a so-called energy ratio during an inspiratory or an expiratory phase each standardized to individual time units, so that such an energy ratio quotient can be compared with an energy ratio threshold value, wherein if this threshold value is exceeded, the trigger information TIE on the basis of the EMG signals is used and if the threshold value is fallen short, the trigger information TIE on the basis of the breathing signal AS is used.

Figure 22:
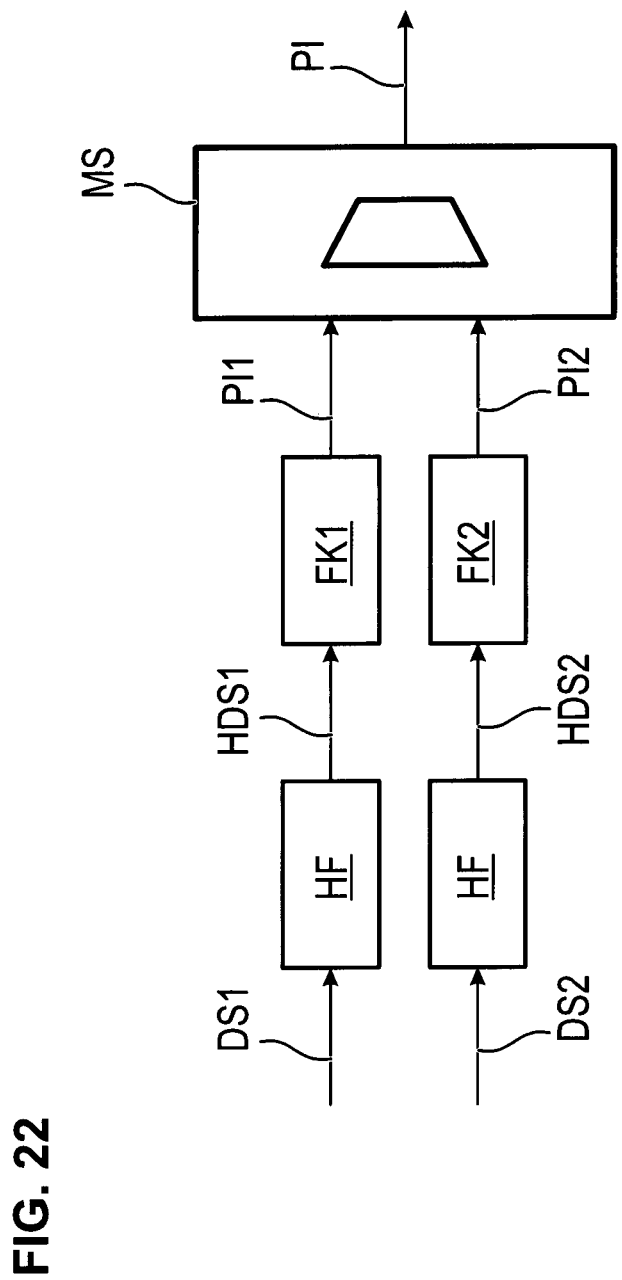
FIG. 22 is a schematic view showing steps for the determination of pressure information in order to select a ventilation pressure as a function of at least one data signal within the framework of a pressure-controlled ventilation support.

FIG. 22 shows steps for obtaining pressure information PI, which likewise can be obtained by the computer R2 of FIG. 20 in order to then actuate the ventilator BG as a function of the pressure information PI. The computer R2 is configured here to check the ventilator BG for a pressure-controlled ventilation support. The pressure-controlled ventilation support of the ventilator BG takes place such that a ventilation pressure takes place at least at times as a function of the obtained at least one data signal DS1, preferably both signals DS1 and DS2. The ventilation support preferably takes place such that the ventilation pressure is proportional to the envelope curve of the at least one data signal HDS1. In this case, the filtered signal HDS1 is obtained from the at least one data signal DS1 by means of Hull filtering HF, as described before. Pressure information PI1 is then obtained from the Hull-filtered signal HDS1 in a function determination step FK1. The pressure information PI can then be formed in a multiplexing step MS on the basis of the pressure information PI1 obtained. For example, the pressure information PI is identical to the pressure information PI1. In this case, the multiplexing step MS consists of a simple mapping of the pressure information PI1 onto the information PI. This information PI may then be provided to the ventilator BG as shown in FIG. 20, or the actuation of the ventilator BG takes place by the computer R2 as a function of the pressure information PI obtained, as mentioned before.

According to FIG. 22, additional pressure information PI2 corresponding to the obtaining of the pressure information PI1 from the data signal DS1 may preferably also be obtained from the data signal DS2. In the multiplexing step MS, the pressure information PI may now be obtained on the basis of both pressure information PI1 and PI2, which are based on the respective data signals DS1 and DS2. Here, pressure information PI2 may thus also preferably be used within the framework of an expiratory phase. Thus, the pressure information PI can carry out a pressure-controlled ventilation as a function of the pressure information obtained or as a function of the two data signals DS1 and DS2 to control the ventilator BG from FIG. 20 both preferably in inspiratory and expiratory phases.

Provisions may also be made here to select the positive end expiratory pressure (PEEP) on the basis of the pressure information PI and to control the ventilator BG as a function of the PEEP value thus obtained. Further, other parameters of time control may also be selected as a function of the pressure information PI.

An adaptation or increase in the base flow during the inhalation and an adaptation or lowering of the base flow during the exhalation may preferably also be selected with knowledge of the pressure information PI.

The data signals DS1 and DS2 obtained are preferably analyzed for establishing a possible change in the respiratory muscle recruiting in order to detect an urgent exhaustion of the respiratory muscle at an early time.

Even though some aspects were described in connection with a device, it is obvious that these aspects also represent a description of the corresponding process, so that a block or a component of a device may also be defined as a corresponding process step or as a feature of a process step. Analogously hereto, aspects that were described in connection with a process step or as a process step also represent a description of a corresponding block or detail or feature of a corresponding device.

Depending on certain implementation requirements, exemplary embodiments of the present invention, the computer may be implemented in hardware and/or in software. An implementation of the mentioned computer may be carried out here as at least one computer or else by a plurality of computers in the network. The implementation may be carried out with the use of a digital storage medium, for example, a floppy disk, a DVD, a Blu-Ray disk, a CD, a ROM, a PROM, an EPROM, an EERPROM or a FLASH memory, a hard drive or another magnetic or optical memory, on which electronically readable control signals, which can or do interact with a programmable hardware component such that the respective process is carried out, are stored.

A programmable hardware component may be formed as a computer by a processor, a computer processor (CPU=Central Processing Unit), a computer, a computer system, an application-specific integrated circuit (ASIC=Application-Specific Integrated Circuit), an integrated circuit (IC=Integrated Circuit), a System on Chip (SOC), a programmable logic component or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes being described here is carried out. An exemplary embodiment is consequently a data storage medium (or a digital storage medium or a computer-readable medium), on which the program for carrying out one of the processes being described here is recorded.

Switches, e.g., those in FIG. 21b, are shown here only conceptually. It is understood that such a switching logic can be embodied by hardware and/or software.

Exemplary embodiments of the present invention may generally be implemented as program, firmware, computer program or computer program product with a program code or as data, wherein the program code or the data act so as to carry out one of the processes when the program is running on a processor or on a programmable hardware component. The program code or the data may also be stored, for example, on a machine-readable medium or data storage medium. The program code or the data may occur, among other things, as source code, machine code or byte code as well as other intermediate code.

Another exemplary embodiment is, furthermore, a data stream, a signal sequence or a sequence of signals, which data stream or sequence represents the program for carrying out one of the processes described herein. The data stream, the signal sequence or the sequence of signals may be configured, for example, such as to be transferred via a data communication link, for example, via the internet or another network. Exemplary embodiments are thus also signal sequences representing data, which are suitable for transmission via a network or a data communication link, wherein the data represent the program.

A program according to an exemplary embodiment may implement one of the processes during its execution, for example, by reading storage locations or by writing a datum or a plurality of data into these, wherein switching operations or other operations are optionally brought about in transistor structures, in amplifier structures or in other electrical, optical, magnetic components or components operating according to another principle of action. Data, values, sensor values or other information can correspondingly be detected, determined or measured by reading a storage location. A program can therefore detect, determine or measure variables, values, measured variables and other information by reading one or more storage locations as well as bring about, prompt or carry out an action as well as actuate other devices, machines and components by writing to one or more storage locations.

While specific embodiments of the invention have been shown and described in detail to illustrate the application of the principles of the invention, it will be understood that the invention may be embodied otherwise without departing from such principles.

The invention claimed is:

1. A device for providing at least one first data signal and one second data signal, wherein the first data signal indicates an activity of at least one muscle of a patient that is relevant for an inspiratory breathing effort and wherein the second data signal indicates an activity of at least one muscle of the patient that is relevant for an expiratory breathing effort, the device comprising:
   a first interface configured to detect at least three or more than three electromyography signals of particular surface electromyography sensor pairs;
   a second interface configured to detect a breathing signal, which indicates a breathing activity of the patient;

a computer configured:
to determine breathing phase information on the basis of the breathing signal, which indicates first time windows of inspiratory breathing activity and second time windows of expiratory breathing activity;
to determine at least three separated signals on the basis of the electromyography signals;
to check whether a heart signal component is detectable in one of the separated signals and to select the corresponding separated signal if a heart signal component is successfully detected; and
to determine the data signals by assigning at least one subset of the remaining separated signals to an inspiratory breathing activity as well as assigning at least one subset of the remaining separated signals to an expiratory breathing activity of the patient as a function of the breathing phase information, wherein one or more signals having the heart component is completely ignored from consideration in determining the data signals; and
a data interface configured to provide the data signals.

2. A device in accordance with claim 1, further comprising:
a display interface configured to output display data to a display unit as a function of the data signals.

3. A device in accordance with claim 1, further comprising a ventilator for ventilating the patient, wherein the computer is further configured to actuate the ventilator as a function of at least one of the data signals.

4. A device in accordance with claim 3, wherein:
the computer is further configured to actuate the ventilator both as a function of the at least one data signal and as a function of the breathing signal;
the computer is further configured to carry out a quality evaluation of the at least one data signal; and
the computer uses either the at least one data signal or the breathing signal as a function of the quality evaluation to actuate the ventilator.

5. A device in accordance with claim 3, wherein:
the computer is further configured to check the ventilator for a pressure-controlled ventilation support; and
the pressure-controlled ventilation support takes place such that a ventilation pressure is carried out at least at times as a function of the at least one data signal.

6. A device in accordance with claim 1, wherein:
the breathing signal is a volume flow signal; and
the computer is further configured to determine the breathing phase information as a function of the volume flow signal and of at least one preset threshold value.

7. A device in accordance with claim 1, wherein the computer is further configured to determine the separated signals by adaptive digital filtering of the electromyography signals.

8. A device in accordance with claim 1, wherein inhalation by the patient takes place during the first time windows of inspiratory breathing activity and exhalation by the patient takes place during the second time windows of expiratory breathing activity.

9. A device in accordance with claim 1, wherein the breathing signal is a volume flow signal.

10. A process for providing at least one first data signal and one second data signal, wherein the first data signal indicates an activity of at least one muscle that is relevant for an inspiratory breathing effort and wherein the second data signal indicates an activity of at least one muscle that is relevant for an expiratory breathing effort, the process comprising the steps of:
detecting three or more than three electromyography signals of particular surface electromyography sensor pairs;
detecting a breathing signal, which indicates a breathing activity of the patient;
determining breathing phase information, on the basis of the breathing signal, which information indicates first time windows of inspiratory breathing activity and second time windows of expiratory breathing activity;
determining at least three separated signals on the basis of the electromyography signals;
checking whether a heart signal component is detectable in one of the at least three separated signals and selecting the corresponding separated signal if a heart signal component is successfully detected;
determining the data signals by assignment of at least one subset of the remaining separated signals to an inspiratory breathing activity and to an expiratory breathing activity of the patient as a function of the breathing phase information, wherein each signal having the heart signal component is not considered when determining the data signals; and
providing the data signals.

11. A process in accordance with claim 10, further comprising the step of outputting display data to an optical display unit as a function of the data signals provided.

12. A process in accordance with claim 10, further comprising the step of controlling a ventilator as a function of at least one of the provided data signals.

13. A process in accordance with claim 10, wherein inhalation by the patient takes place during the first time windows of inspiratory breathing activity and exhalation by the patient takes place during the second time windows of expiratory breathing activity.

14. A process in accordance with claim 10, wherein the breathing signal is a volume flow signal.

15. A program comprising a program code for executing on a computer, a processor or a programmable hardware component a process comprising the steps of:
detecting three or more than three electromyography signals of particular surface electromyography sensor pairs;
detecting a breathing signal, which indicates a breathing activity of the patient;
determining breathing phase information based on the breathing signal, which information indicates first time windows of inspiratory breathing activity and second time windows of expiratory breathing activity;
determining at least three separated signals on the basis of the electromyography signals;
checking whether a heart signal component is detectable in one of the at least three separated signals and selecting the corresponding separated signal if a heart signal component is successfully detected;
determining data signals by assigning at least one subset of the remaining separated signals to an inspiratory breathing activity of the patient and assigning at least one subset of the remaining separated signals to an expiratory breathing activity of the patient as a function of the breathing phase information, wherein each signal having the heart signal component is completely ignored from consideration in determining the data signals; and providing the determined data signals, wherein the first data signal indicates an activity of at least one muscle that is relevant for an inspiratory breathing effort and the second data signal indicates an activity of at least one muscle that is relevant for an expiratory breathing effort.

16. A program in accordance with claim 15, wherein the process further comprises the step of outputting display data to an optical display unit as a function of the data signals provided.

17. A program in accordance with claim 15, wherein the process further comprises the step of controlling a ventilator as a function of at least one of the provided data signals.

18. A program in accordance with claim 15, wherein inhalation by the patient takes place during the first time windows of inspiratory breathing activity and exhalation by the patient takes place during the second time windows of expiratory breathing activity.

19. A program in accordance with claim 15, wherein the breathing signal is a volume flow signal.

* * * * *